(12) United States Patent
Tozawa et al.

(10) Patent No.: US 7,176,010 B2
(45) Date of Patent: Feb. 13, 2007

(54) ISOLATED HUMAN PROTEIN HAVING ESTERASE ACTIVITY AND DNA ENCODING THE SAME

(75) Inventors: Ryuichi Tozawa, Toyonaka (JP); Eiji Sunahara, Ibaraki (JP); Yoshio Taniyama, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/343,141

(22) PCT Filed: Aug. 8, 2001

(86) PCT No.: PCT/JP01/06827

§ 371 (c)(1),
(2), (4) Date: Jan. 28, 2003

(87) PCT Pub. No.: WO02/14512

PCT Pub. Date: Feb. 21, 2002

(65) Prior Publication Data

US 2004/0102371 A1   May 27, 2004

(30) Foreign Application Priority Data

Aug. 10, 2000 (JP) ............................. 2000-247967
Aug. 30, 2000 (JP) ............................. 2000-266005
Jun. 12, 2001 (JP) ............................. 2001-177739

(51) Int. Cl.
  *C12N 9/18*    (2006.01)
  *C12Q 1/44*    (2006.01)
  *C07K 14/00*   (2006.01)
  *C12N 1/20*    (2006.01)
  *C12N 15/00*   (2006.01)
  *C12N 5/00*    (2006.01)
  *C12P 21/06*   (2006.01)
  *C07H 21/04*   (2006.01)
  *A61K 38/46*   (2006.01)

(52) U.S. Cl. .................. 435/197; 435/19; 435/69.1; 435/320.1; 435/325; 435/252.3; 530/350; 536/23.2; 536/23.5; 424/94.6

(58) Field of Classification Search ............... 435/197, 435/19, 69.1, 320.1, 325, 252.3; 530/530, 530/350; 536/23.2, 23.5; 424/94.6

See application file for complete search history.

(56) References Cited

OTHER PUBLICATIONS

Witkowski et al. , Biochemistry 38:11643-11650, 1999.*
Seffernick et al. , J. Bacteriol. 183(8):2405-2410, 2001.*
Broun et al. , Science 282:1315-1317, 1998.*
Probst et al., EMBL accession No. AAA35551, 1994.*
Guo et al., PNAS 101(25):9205-9210, 2004.*
Probst, et al. "Human Liver Arylacetamide Deacetylase" The Journal of Biological Chemistry 269(34): 21650-21656 (1994).

* cited by examiner

*Primary Examiner*—Rebecca Prouuty
*Assistant Examiner*—Delia M. Ramirez
(74) *Attorney, Agent, or Firm*—Mark Chao; Elaine M. Ramesh

(57) ABSTRACT

The present invention provides novel esterase proteins, Specifically, the present invention provides proteins having the same or substantially the same amino acid sequence as the amino acid sequence represented by SEQ ID NO: 1 or SEQ ID NO: 7, or salts thereof; their partial peptides or salts thereof: DNAs encoding the proteins; recombinant vectors containing the DNAs; transformants, a method of manufacturing the proteins; pharmaceuticals comprising the proteins or DNAs; antibodies to the proteins; a method of screening compounds or salts thereof having an activity of promoting the esterase activity of the proteins; the compounds obtained by the screening; and pharmaceuticals comprising the said compounds; etc.

3 Claims, 2 Drawing Sheets

```
                        SEQUENCE LISTING

<160> NUMBER OF SEQ ID NOS: 12

<210> SEQ ID NO 1
<211> LENGTH: 401
<212> TYPE: PRT
<213> ORGANISM: Human

<400> SEQUENCE: 1

Met Gly Leu Lys Ala Leu Cys Leu Gly Leu Leu Cys Val Leu Phe Val
                 5                  10                  15

Ser His Phe Tyr Thr Pro Met Pro Asp Asn Ile Glu Glu Ser Trp Lys
             20                  25                  30

Ile Met Ala Leu Asp Ala Ile Ala Lys Thr Cys Thr Phe Thr Ala Met
         35                  40                  45

Cys Phe Glu Asn Met Arg Ile Met Arg Tyr Glu Glu Phe Ile Ser Met
     50                  55                  60

Ile Phe Arg Leu Asp Tyr Thr Gln Pro Leu Ser Asp Glu Tyr Ile Thr
 65                  70                  75                  80

Val Thr Asp Thr Thr Phe Val Asp Ile Pro Val Arg Leu Tyr Leu Pro
                 85                  90                  95

Lys Arg Lys Ser Glu Thr Arg Arg Ala Val Ile Tyr Phe His Gly
             100                 105                 110

Gly Gly Phe Cys Phe Gly Ser Ser Lys Gln Arg Ala Phe Asp Phe Leu
         115                 120                 125

Asn Arg Trp Thr Ala Asn Thr Leu Asp Ala Val Val Val Gly Val Asp
     130                 135                 140

Tyr Arg Leu Ala Pro Gln His His Phe Pro Ala Gln Phe Glu Asp Gly
145                 150                 155                 160

Leu Ala Ala Val Lys Phe Phe Leu Leu Glu Lys Ile Leu Thr Lys Tyr
                 165                 170                 175

Gly Val Asp Pro Thr Arg Ile Cys Ile Ser Gly Asp Ser Ser Gly Gly
             180                 185                 190
```

```
            Asn Leu Ala Thr Ala Val Thr Gln Gln Val Gln Asn Asp Ala Glu Ile
                195                 200                 205
            Lys His Lys Ile Lys Met Gln Val Leu Leu Tyr Pro Gly Leu Gln Ile
                210                 215                 220
            Thr Asp Ser Tyr Leu Pro Ser His Arg Glu Asn Glu His Gly Ile Val
            225                 230                 235                 240
            Leu Thr Arg Asp Val Ala Ile Lys Leu Val Ser Leu Tyr Phe Thr Lys
                                245                 250                 255
            Asp Glu Ala Leu Pro Trp Ala Met Arg Arg Asn Gln His Met Pro Leu
                            260                 265                 270
            Glu Ser Arg His Leu Phe Lys Phe Val Asn Trp Ser Ile Leu Leu Pro
                        275                 280                 285
            Glu Lys Tyr Arg Lys Asp Tyr Val Tyr Thr Glu Pro Ile Leu Gly Gly
                    290                 295                 300
            Leu Ser Tyr Ser Leu Pro Gly Leu Thr Asp Ser Arg Ala Leu Pro Leu
            305                 310                 315                 320
            Leu Ala Asn Asp Ser Gln Leu Gln Asn Leu Pro Leu Thr Tyr Ile Leu
                                325                 330                 335
            Thr Cys Gln His Asp Leu Leu Arg Asp Asp Gly Leu Met Tyr Val Thr
                            340                 345                 350
            Arg Leu Arg Asn Val Gly Val Gln Val His Glu His Ile Glu Asp
                        355                 360                 365
            Gly Ile His Gly Ala Leu Ser Phe Met Thr Ser Pro Phe Tyr Leu Arg
                    370                 375                 380
            Leu Gly Leu Arg Ile Arg Asp Met Tyr Val Ser Trp Leu Asp Lys Asn
            385                 390                 395                 400
            Leu

<210> SEQ ID NO 2
<211> LENGTH: 1203
<212> TYPE: DNA
<213> ORGANISM: Human

<400> SEQUENCE: 2 atgggctaa aagctctctg tttggggctg ctttgtgttc ttttttgtctc tcatttttac     60
acacccatgc cagacaacat tgaagaaagc tggaaaataa tggccttgga tgccatcgct    120
aaaacttgta catttacggc tatgtgtttt gaaaatatgc gtattatgag atatgaagag    180
tttatatcca tgatattcag gctggattat acccaaccac tttcagatga atacatcaca    240
gtgactgata caacatttgt tgacattcca gtacgattgt acttgccaaa agaaagtca    300
gaaacccgaa ggcgagctgt gatatatttt catggtggtg ttttttgttt tggaagttcc    360
aaacagaggg cttttgactt cctgaataga tggacggcaa acacgcttga tgctgttgtt    420
gtaggcgtgg actataggct ggctcctcaa caccactttc ctgctcagtt tgaagatggc    480
cttgctgcag tcaatttttt tcttttggaa aaaattctta caaaatatgg agtggatccc    540
acccgaatct gcatttcggg agacagttct ggggcaatt tagcaacagc ggtcactcaa    600
caggtgcaga tgatgctga ataaaacat aaaatcaaga tgcaagtctt actttaccct    660
ggcttacaga taacagattc ttatttgcca tctcaccgag aaaatgagca tggtatagtt    720
ttgaccaggg atgtagccat aaaactcgtg agcttatatt tcaccaagga tgaagcactt    780
ccctgggcaa tgagaagaaa ccaacacatg cctctggagt caagacatct gtttaagttt    840
gttaactgga gtattcttct tcctgagaag tatagaaaag actatgtata tactgaacca    900
```

```
attcttggag gacttagtta ttcattgcca ggacttacag acagcagagc attacccttg    960
ttggccaatg attctcagtt acagaatttg ccactaacct atattcttac ttgtcaacat   1020
gatctcttaa gagatgatgg acttatgtat gttacaagac ttcgaaatgt tggagtccaa   1080
gttgttcatg aacatattga ggatggaatt catggagctt tatcattcat gacttcacca   1140
ttttatttac gtctaggtct taggataaga gatatgtatg taagttggct ggataagaat   1200
tta                                                                 1203

<210> SEQ ID NO 3
<211> LENGTH: 27
<212> TYPE: DNA
<213> ORGANISM: Artificial Sequence
<220> FEATURE:
<223> OTHER INFORMATION: Designed oligonucleotide primer to amplify DNA
      encoding LIP-1

<400> SEQUENCE: 3
caagtctaca  attgctctac  tagttac                                       27

<210> SEQ ID NO 4
<211> LENGTH: 25
<212> TYPE: DNA
<213> ORGANISM: Artificial Sequence
<220> FEATURE:
<223> OTHER INFORMATION: Designed oligonucleotide primer to amplify DNA
      encoding LIP-1

<400> SEQUENCE: 4
tccactatgt aagggctata catac                                           25

<210> SEQ ID NO 5
<211> LENGTH: 18
<212> TYPE: DNA
<213> ORGANISM: Artificial Sequence
<220> FEATURE:
<223> OTHER INFORMATION: Designed oligonucleotide primer to amplify DNA
      encoding LIP-1

<400> SEQUENCE: 5
atgccatcgc taaaactt                                                   18

<210> SEQ ID NO 6
<211> LENGTH: 18
<212> TYPE: DNA
<213> ORGANISM: Artificial Sequence
<220> FEATURE:
<223> OTHER INFORMATION: Designed oligonucleotide primer to amplify DNA
      encoding LIP-1

<400> SEQUENCE: 6
gaactgtctc ccgaaatg                                                   18

<210> SEQ ID NO 7
<211> LENGTH: 401
<212> TYPE: PRT
<213> ORGANISM: Human

<400> SEQUENCE: 7

Met Gly Leu Lys Ala Leu Cys Leu Gly Leu Leu Cys Val Leu Phe Val
                 5                  10                  15

Ser His Phe Tyr Thr Pro Met Pro Asp Asn Ile Glu Glu Ser Trp Lys
             20                  25                  30

Ile Met Ala Leu Asp Ala Ile Ala Lys Thr Cys Thr Phe Thr Ala Met
```

```
                35                  40                  45
Cys Phe Glu Asn Met Arg Ile Met Arg Tyr Glu Glu Phe Ile Ser Met
        50                  55                  60

Ile Phe Arg Leu Asp Tyr Thr Gln Pro Leu Ser Asp Glu Tyr Ile Thr
 65                  70                  75                  80

Val Thr Asp Thr Thr Phe Val Asp Ile Pro Val Arg Leu Tyr Leu Pro
                85                  90                  95

Lys Arg Lys Ser Glu Thr Arg Arg Ala Val Ile Tyr Phe His Gly
               100                 105                 110

Gly Gly Phe Cys Phe Gly Ser Ser Lys Gln Arg Ala Phe Asp Phe Leu
               115                 120                 125

Asn Arg Trp Thr Ala Asn Thr Leu Asp Ala Val Val Gly Val Asp
130                 135                 140

Tyr Arg Leu Ala Pro Gln His His Phe Pro Ala Gln Phe Glu Asp Gly
145                 150                 155                 160

Leu Ala Ala Val Lys Phe Phe Leu Leu Glu Lys Ile Leu Thr Lys Tyr
                    165                 170                 175

Gly Val Asp Pro Thr Arg Ile Cys Ile Ala Gly Asp Ser Ser Gly Gly
                180                 185                 190

Asn Leu Ala Thr Ala Val Thr Gln Gln Val Gln Asn Asp Ala Glu Ile
                195                 200                 205

Lys His Lys Ile Lys Met Gln Val Leu Leu Tyr Pro Gly Leu Gln Ile
210                 215                 220

Thr Asp Ser Tyr Leu Pro Ser His Arg Glu Asn Glu His Gly Ile Val
225                 230                 235                 240

Leu Thr Arg Asp Val Ala Ile Lys Leu Val Ser Leu Tyr Phe Thr Lys
                    245                 250                 255

Asp Glu Ala Leu Pro Trp Ala Met Arg Arg Asn Gln His Met Pro Leu
                260                 265                 270

Glu Ser Arg His Leu Phe Lys Phe Val Asn Trp Ser Ile Leu Leu Pro
                275                 280                 285

Glu Lys Tyr Arg Lys Asp Tyr Val Tyr Thr Glu Pro Ile Leu Gly Gly
                290                 295                 300

Leu Ser Tyr Ser Leu Pro Gly Leu Thr Asp Ser Arg Ala Leu Pro Leu
305                 310                 315                 320

Leu Ala Asn Asp Ser Gln Leu Gln Asn Leu Pro Leu Thr Tyr Ile Leu
                    325                 330                 335

Thr Cys Gln His Asp Leu Leu Arg Asp Asp Gly Leu Met Tyr Val Thr
                340                 345                 350

Arg Leu Arg Asn Val Gly Val Gln Val Val His Glu His Ile Glu Asp
                355                 360                 365

Gly Ile His Gly Ala Leu Ser Phe Met Thr Ser Pro Phe Tyr Leu Arg
370                 375                 380

Leu Gly Leu Arg Ile Arg Asp Met Tyr Val Ser Trp Leu Asp Lys Asn
385                 390                 395                 400

Leu

<210> SEQ ID NO 8
<211> LENGTH: 1203
<212> TYPE: DNA
<213> ORGANISM: Human

<400> SEQUENCE: 8
atggggctaa aagctctctg tttggggctg ctttgtgttc tttttgtctc tcattttac     60
```

```
acacccatgc cagacaacat tgaagaaagc tggaaaataa tggccttgga tgccatcgct    120
aaaacttgta catttacggc tatgtgtttt gaaaatatgc gtattatgag atatgaagag    180
tttatatcca tgatattcag gctggattat acccaaccac tttcagatga atacatcaca    240
gtgactgata caacatttgt tgacattcca gtacgattgt acttgccaaa agaaagtca    300 gaaacccgaa ggcgagctgt gatatatttt catggtggtg ttttttgttt tggaagttcc    360
aaacagaggg cttttgactt cctgaataga tggacggcaa acacgcttga tgctgttgtt    420
gtaggcgtgg actataggct ggctcctcaa caccactttc ctgctcagtt tgaagatggc    480
cttgctgcag tcaaattttt tcttttggaa aaaattctta caaaatatgg agtggatccc    540
acccgaatct gcattgcggg agacagttct gggggcaatt tagcaacagc ggtcactcaa    600
caggtgcaga atgatgctga ataaaaacat aaaatcaaga tgcaagtctt actttaccct    660
ggcttacaga taacagattc ttatttgcca tctcaccgag aaaatgagca tggtatagtt    720
ttgaccaggg atgtagccat aaaactcgtg agcttatatt tcaccaagga tgaagcactt    780
ccctgggcaa tgagaagaaa ccaacacatg cctctggagt caagacatct gtttaagttt    840
gttaactgga gtattcttct tcctgagaag tatagaaaag actatgtata tactgaacca    900
attcttggag gacttagtta ttcattgcca ggacttacag acagcagagc attacccttg    960
ttggccaatg attctcagtt acagaatttg ccactaacct atattcttac ttgtcaacat   1020
gatctcttaa gagatgatgg acttatgtat gttacaagac ttcgaaatgt tggagtccaa   1080
gttgttcatg aacatattga ggatggaatt catggagctt tatcattcat gacttcacca   1140
ttttatttac gtctaggtct taggataaga gatatgtatg taagttggct ggataagaat   1200
tta                                                                1203

<210> SEQ ID NO 9
<211> LENGTH: 27
<212> TYPE: DNA
<213> ORGANISM: Artificial Sequence
<220> FEATURE:
<223> OTHER INFORMATION: Designed oligonucleotide primer to amplify DNA
                        encoding mLIP-1

<400> SEQUENCE: 9
atgggattca aagctctctg ttttgga                                        27

<210> SEQ ID NO 10
<211> LENGTH: 27
<212> TYPE: DNA
<213> ORGANISM: Artificial Sequence
<220> FEATURE:
<223> OTHER INFORMATION: Designed oligonucleotide primer to amplify DNA
                        encoding mLIP-1

<400> SEQUENCE: 10
tatccacaaa aattaggtta tgagaca                                        27

<210> SEQ ID NO 11
<211> LENGTH: 1203
<212> TYPE: DNA
<213> ORGANISM: Mouse

<400> SEQUENCE: 11
atgggattca aagctctctg ttttggactg ctttgtgtta gcttttttatc ttgtatttat    60 acacccgtgc ctgacaacat tgaagaaacc tggaaagtaa tggctttgga tacagttgct   120
```

-continued

```
aaaacttgtt cccttatggc tttgtgtctt gaaaacttag gtgtcatgag atatgaagaa    180
tttatctcca tgataatcaa tctggattac acacaaccgc tttctgatga acacatcaca    240
gtaaccgata ctgcctttgt tgacattcct gtgcgtttgt accttcccaa gagaaagtca    300
gaagccccaa gacgagctgt gatctatttt catggaggag gttttgttt cgggagtttt     360
aagcagaggg cttttgattt cctgaataga tggactgcaa acaaacttga cgctgttgtt    420
gtaggaatag actacaggct agcgcctcaa catcacttcc ctgcacaatt tgaagatggt    480
atcacagcag tcaagttttt tcttcaggat aaaattctaa caaagtatgg agtagatcct    540
acccgaattg ctgtgtcagg agacagttct ggaggaactc tggctgcagc ggtgacacaa    600
caggtgcaga ttgatcctga agtaaagcat aaactcaagc tgcaagccct gctttatcct    660
ggcttgcagg tgattgacac tcacttgcca tctcatcgag aaaacgaaca tggcatagtt    720
ctgacaaggg acatagccat aaaacttgtg agtttgtttt tcaccaagga tgaggcactt    780
ccacaggcaa tgagaaaaaa ccagcacatg cctccagagt ccagacatct cttcaggttt    840
gtcaactgga gtactcttct ccctgacaag tttagaaagg accatgtata cactgagcct    900
gtgcttggaa gatcggcttt ctccctgcca gcgctgatgg accacagagc attgcccttg    960
ttagccagtg atgaccactt acagcacttg ccacaaacat acattcttac ctgtcaacat   1020
gatgtcctga gagatgatgg gatcatgtat gtttcaagac ttcaaaaggt tggagtccaa   1080
gttttccatg accatgttga ggatggaatc cacggagcct atcatatat gacatcgcca    1140
cttcacttag atctagggct gaggataaaa gatatgtatg ttagttggct ggataataat   1200
tta                                                                 1203
```

<210> SEQ ID NO 12
<211> LENGTH: 401
<212> TYPE: PRT
<213> ORGANISM: Mouse

<400> SEQUENCE: 12

```
Met Gly Phe Lys Ala Leu Cys Phe Gly Leu Leu Cys Val Ser Phe Leu
              5                  10                  15

Ser Cys Ile Tyr Thr Pro Val Pro Asp Asn Ile Glu Glu Thr Trp Lys
         20                  25                  30

Val Met Ala Leu Asp Thr Val Ala Lys Thr Cys Ser Leu Met Ala Leu
     35                  40                  45

Cys Leu Glu Asn Leu Gly Val Met Arg Tyr Glu Glu Phe Ile Ser Met
 50                  55                  60

Ile Ile Asn Leu Asp Tyr Thr Gln Pro Leu Ser Asp Glu His Ile Thr
65                  70                  75                  80

Val Thr Asp Thr Ala Phe Val Asp Ile Pro Val Arg Leu Tyr Leu Pro
                 85                  90                  95

Lys Arg Lys Ser Glu Ala Pro Arg Arg Ala Val Ile Tyr Phe His Gly
            100                 105                 110

Gly Gly Phe Cys Phe Gly Ser Phe Lys Gln Arg Ala Phe Asp Phe Leu
        115                 120                 125

Asn Arg Trp Thr Ala Asn Lys Leu Asp Ala Val Val Gly Ile Asp
    130                 135                 140

Tyr Arg Leu Ala Pro Gln His His Phe Pro Ala Gln Phe Glu Asp Gly
145                 150                 155                 160

Ile Thr Ala Val Lys Phe Phe Leu Gln Asp Lys Ile Leu Thr Lys Tyr
                165                 170                 175
```

-continued

```
Gly Val Asp Pro Thr Arg Ile Ala Val Ser Gly Asp Ser Ser Gly Gly
            180             185             190

Thr Leu Ala Ala Ala Val Thr Gln Gln Val Gln Ile Asp Pro Glu Val
            195             200             205

Lys His Lys Leu Lys Leu Gln Ala Leu Leu Tyr Pro Gly Leu Gln Val
    210             215             220

Ile Asp Thr His Leu Pro Ser His Arg Glu Asn Glu His Gly Ile Val
225             230             235             240

Leu Thr Arg Asp Ile Ala Ile Lys Leu Val Ser Leu Phe Phe Thr Lys
            245             250             255

Asp Glu Ala Leu Pro Gln Ala Met Arg Lys Asn Gln His Met Pro Pro
            260             265             270

Glu Ser Arg His Leu Phe Arg Phe Val Asn Trp Ser Thr Leu Leu Pro
            275             280             285

Asp Lys Phe Arg Lys Asp His Val Tyr Thr Glu Pro Val Leu Gly Arg
        290             295             300

Ser Ala Phe Ser Leu Pro Ala Leu Met Asp His Arg Ala Leu Pro Leu
305             310             315             320

Leu Ala Ser Asp Asp His Leu Gln His Leu Pro Gln Thr Tyr Ile Leu
            325             330             335

Thr Cys Gln His Asp Val Leu Arg Asp Asp Gly Ile Met Tyr Val Ser
            340             345             350

Arg Leu Gln Lys Val Gly Val Gln Val Phe His Asp His Val Glu Asp
            355             360             365

Gly Ile His Gly Ala Leu Ser Tyr Met Thr Ser Pro Leu His Leu Asp
        370             375             380

Leu Gly Leu Arg Ile Lys Asp Met Tyr Val Ser Trp Leu Asp Asn Asn
385             390             395             400

Leu
```

ISOLATED HUMAN PROTEIN HAVING ESTERASE ACTIVITY AND DNA ENCODING THE SAME

This application is the National Phase filing of International Patent Application No. PCT/JP01/06827, filed 08 Aug. 2001.

FIELD OF THE INVENTION

The present invention relates to human adipose tissue-derived lipolytic enzyme proteins or salts thereof, as well as DNAs encoding the proteins.

BACKGROUND ART

It is well established that lipases and esterases serve an important role in digestion or absorption of dietary lipids, degradation or accumulation of lipids in the living body, detoxication or degradation of hazardous compounds, etc. Among others, a hormone-sensitive lipase (hereinafter abbreviated as HSL), expression of which is widely found in tissues including adipose tissues, such as testis, heart, skeletal muscle, pancreas, aorta, etc., has been attracting the attention as a regulatory factor of fat deposits in vivo and energy consumption, glucose metabolism or arteriosclerosis lesion formation (Holm, C. and Osterlund, T. Methods in Molecular Biology, 109, 109–121).

That is, reportedly, HSL as a rate-limiting enzyme for neutral fats (especially triglycerides) in the respective tissues, not only controls the amount of fatty acids supplied, which are utilized for energy production in muscle tissues or brown adipocytes (Himms-Hagen, J. Prog. Lipid Res., 28, 67–115 (1989)) or for ligand production of nuclear receptors or PPARs (Tontonoz, P. et al., Cell, 79, 1147–1156 (1994)) but is also associated with regulation of insulin secretion in pancreatic β cells (Mulder, H. et al., Diabetes, 48, 228–232 (1999)). It has also been suggested that HSL is likely to be associated with the formation of atherosclerosis nest and its retraction as neutral cholesteryl ester hydrolase (hereinafter abbreviated as NCEH) responsible for degradation of intracellular cholesteryl ester (Escarry, J-L et al., Arterioscler. Thromb. Vasc. Biol., 18, 991–998).

However, there is no difference in body weight between HSL-deficient mice prepared by Osuga et al. and wild type mice. Moreover, the hormone-sensitive triglyceride degradation activity in adipocytes or the NCEH activity in macrophages significantly remains in the HSL-deficient mice, while no change is observed in body temperature generation under cold conditions (Osuga, J. et al., Proc. Natl. Acad. Sci. USA, 97, 787–792 (2000)). It is thus strongly suggested that another HSL-like lipase or esterase would participate in various lipolysis processes hitherto considered to be associated with HSL, and such a lipase or esterase is engaged in fatty acid production in adipocytes or muscle tissues or foam cell formation in macrophages, with expectation that the lipase or esterase is likely to play an important role in the development of arteriosclerosis, hyperlipidemia, mellitus diabetes, obesity, etc.

So far it is known that enzymes, which has been reported to express neutral lipid degradation enzymes in adipose tissues, aorta or macrophages, include a bile salt activation lipase (Li, F. and Hui, D. Y., J. Biol. Chem., 272, 28666–18671 (1997)), a lipoprotein lipase (Mattsson, L. et al., J. Clin. Invest., 92, 1759–1765 (1993)), monocyte/macrophage serine esterase I (Zschunke, F. et al., Blood, 78, 506–512 (1991)), an endothelium-derived lipase (Jaye, M. et al., Nature Genet., 21, 424–428 (1999)), a lysosome acidic lipase (Sakurada, T. et al., Biochim. Biophys. Acta, 424, 204–212 (1976)), etc. However, it makes no sense at all that any of these enzymes would be replaceable for the functions of HSL in view of localization in tissues/cells, substrate specificity, optimum pH for the activities, presence or absence of hormone sensitivity, activity variation patterns during the course of foam cell formation of macrophages, etc. It has thus been desired to isolate a novel lipase or esterase derived from adipocytes or macrophages.

The present invention provides novel proteins having an esterase activity, in particular, a triglyceride degradation activity, etc., partial peptides or salts thereof, DNAs encoding the proteins, recombinant vectors, transformants, methods of manufacturing the proteins, drugs comprising the proteins or DNAs, antibodies to the proteins, screening methods/screening kits for compounds having the activity of promoting the esterase activity of the proteins, compounds obtained by the screening methods, pharmaceuticals comprising the compounds above, etc.

DISCLOSURE OF THE INVENION

As amino acid sequences characteristic of HSL and its analogous lipase or esterase, GXSXG sequence and HG (or HGG, HGGG) sequence located upstream are known (Harri, H. et al., Biochim. Biophys. Acta, 1210, 249–253 (1994)). Paying attention to these sequences, the present inventors made strenuous search for genes, which expression is recognized in adipose tissues or macrophages, and as a result, a novel gene for lipolytic enzymes as stated in the present invention have found. This gene is recognized to be expressed in adipose tissues, macrophages and skeletal muscle, and thus expected to function as a neutral lipid degradation enzyme substitutable for HSL. Also, animals in which expression of the gene is modified are not only useful as novel model animals with arteriosclerosis, hyperlipidemia, obesity or mellitus diabetes. Moreover, pharmaceuticals, which are affected to the expression of the gene and the activities of the proteins encoded by the gene, are useful as drugs for the treatment of arteriosclerosis, hyperlipidemia, obesity or mellitus diabetes, based on a novel mechanism.

That is, the present invention provides:

(1) A protein containing the same or substantially the same amino acid sequence as the amino acid sequence represented by SEQ ID NO: 1 or SEQ ID NO: 7, or a salt thereof;

(2) The protein or its salt according to (1), wherein substantially the same amino acid sequence represented by SEQ ID NO: 1 or SEQ ID NO: 7 is an amino acid sequence having homology of at least about 75% to the amino acid sequence represented by SEQ ID NO: 1 or SEQ ID NO: 7;

(3) The protein or its salt according to (1), which contains the amino acid sequence represented by SEQ ID NO: 1;

(4) The protein or its salt according to (1), which contains the amino acid sequence represented by SEQ ID NO: 7;

(5) The protein or its salt according to (1), which contains the amino acid sequence represented by SEQ ID NO: 12;

(6) A partial peptide of the protein according to (1), or a salt thereof;

(7) The protein or its salt according to (1) through (5) or the partial peptide or its salt according to (6), which has an esterase activity;

(8) The protein or its salt according to (1) through (5) or the partial peptide or its salt according to (6), which has a triglyceride degradation activity;

(9) A polynucleotide containing a polynucleotide encoding the protein according to (1);

(10) The polynucleotide according to (9), which is a DNA;

(11) The DNA according to (10) containing the base sequence represented by SEQ ID NO: 2 or SEQ ID NO: 8;

(12) The DNA according to (10) containing the base sequence represented by SEQ ID NO: 11;

(13) A recombinant vector containing the polynucleotide according to (9);

(14) A transformant transformed by the recombinant vector according to (13);

(15) A method of manufacturing the protein or its salt according to (1), which comprises culturing the transformant according to (14), and producing and accumulating the protein or its salt according to (1);

(16) A pharmaceutical comprising the protein or its salt according to (1);

(17) A pharmaceutical comprising the polynucleotide according to (9);

(18) The pharmaceutical according to (16) or (17), which is a prophylactic/therapeutic agent for arteriosclerosis, hyperlipidemia, obesity or mellitus diabetes;

(19) An antibody to the protein according to (1), the partial peptide according to (6), or salts thereof;

(20) A method of screening a compound or its salt that promotes or inhibits the esterase activity of the protein according to (1) or the partial peptide according to (6), or salts thereof, which comprises using the protein according to (1) or the partial peptide according to (6), or salts thereof;

(21) A kit for screening a compound or its salt that promotes or inhibits the esterase activity of the protein according to (1) or the partial peptide according to (6), or a salt thereof, comprising the protein according to (1) or the partial peptide according to (6), or a salt thereof;

(22) A compound or its salt that promotes or inhibits the esterase activity of the protein according to (1) or the partial peptide according to (6), or a salt thereof, which is obtainable using the screening method according to (20) or the screening kit according to (21);

(23) A pharmaceutical comprising a compound or its salt that promotes the esterase activity of the protein according to (1) or the partial peptide according to (6), or a salt thereof, which is obtainable using the screening method according to (20) or the screening kit according to (21);

(24) The pharmaceutical according to (23), which is a prophylactic/therapeutic agent for arteriosclerosis, hyperlipidemia, obesity or mellitus diabetes;

(25) A pharmaceutical comprising a compound or its salt that inhibits the esterase activity of the protein according to (1) or the partial peptide according to (6), or a salt thereof, which is obtainable using the screening method according to (20) or the screening kit according to (21);

(26) The pharmaceutical according to (23), which is a prophylactic/therapeutic agent for obesity;

(27) A diagnostic agent comprising the antibody according to (19);

(28) The agent according to (27), which is a diagnostic agent for arteriosclerosis, hyperlipidemia, obesity or mellitus diabetes;

(29) A method for the prevention/treatment of arteriosclerosis, hyperlipidemia, obesity or mellitus diabetes, which comprises administering an effective dose of a compound or its salt that promotes the esterase activity of the protein according to (1) or the partial peptide according to (6), or a salt thereof, which is obtainable using the screening method according to (20) or the screening kit according to (21);

(30) A method for the prevention/treatment of obesity, which comprises administering to a mammal an effective dose of a compound or its salt that inhibits the esterase activity of the protein according to (1) or the partial peptide according to (6), or a salt thereof, which is obtainable using the screening method according to (20) or the screening kit according to (21);

(31) Use of a compound or its salt that promotes the esterase activity of the protein according to (1) or the partial peptide according to (6), or a salt thereof, to manufacture an agent for the prevention/treatment of arteriosclerosis, hyperlipidemia, obesity or mellitus diabetes, which is obtainable using the screening method according to (20) or the screening kit according to (21);

(32) Use of a compound or its salt that inhibits the esterase activity of the protein according to (1) or the partial peptide according to (6), or a salt thereof, to manufacture an agent for the prevention/treatment of arteriosclerosis, hyperlipidemia, obesity or mellitus diabetes, which is obtainable using the screening method according to (20) or the screening kit according to (21); etc.

BEST MODE FOR CARRYING OUT THE INVENTION

Figure 1:
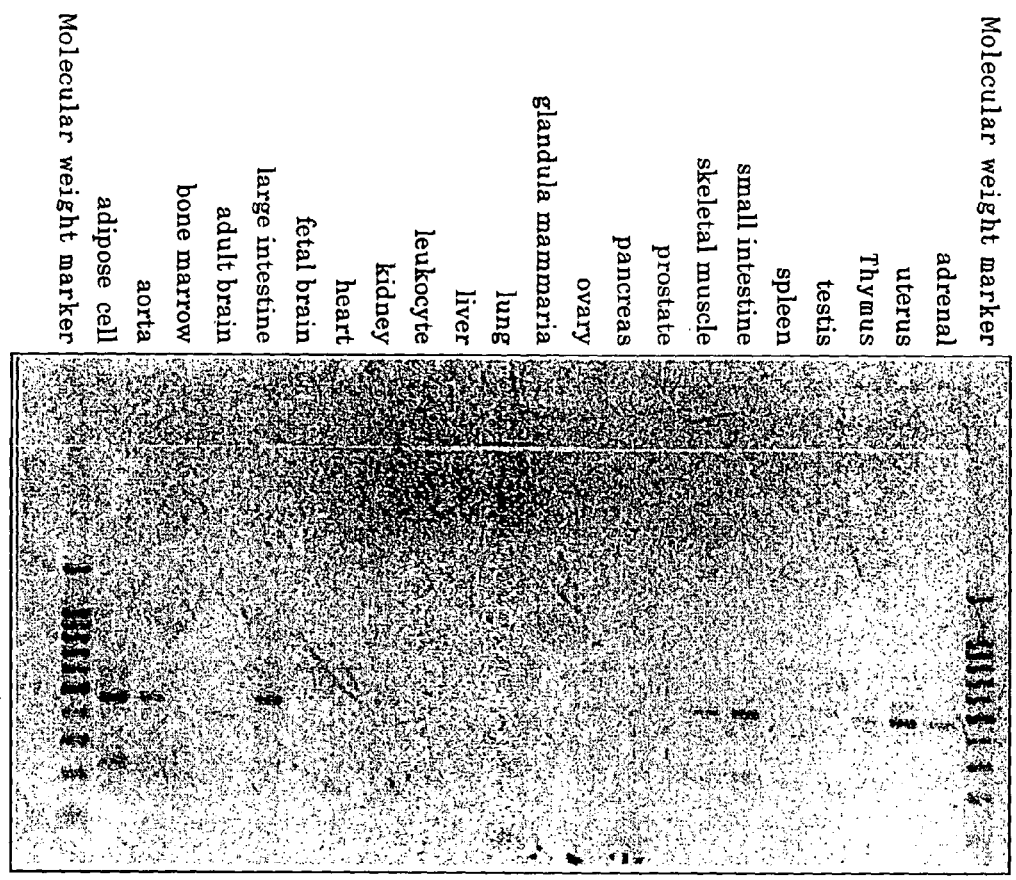
FIG. 1 shows the results of expression distribution of LIP-1 in human tissues.

The protein containing the same or substantially the same amino acid sequence as the amino acid sequence represented by SEQ ID NO: 1 or SEQ ID NO: 7 (hereinafter referred to as the protein of the invention) may be any protein derived from any cells of warm-blooded animals (e.g., human, guinea pig, rat, mouse, chicken, rabbit, swine, sheep, bovine, monkey, etc.) (e.g., hepatocytes, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.); or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel (e.g., aorta), heart, thymus, spleen, submandibular gland, peripheral blood, prostate, testis, ovary, placenta, uterus, bone, joint, skeletal muscle, etc.; or hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); the proteins may also be synthetic proteins.

The amino acid sequence represented by SEQ ID NO: 7 is an amino acid sequence represented by SEQ ID NO: 1, in which the 186th Ser is replaced by Ala.

The amino acid sequence which has substantially the same amino acid sequence as the amino acid sequence represented by SEQ ID NO: 1 or SEQ ID NO: 7 includes amino acid sequences having at least about 55% homology, preferably at least about 60% homology, more preferably at least about 70% homology, much preferably at least about 75%, further much more preferably at least about 80% homology, particularly preferably at least about 90% homology, and most preferably at least about 95% homology, to the amino acid sequence represented by SEQ ID NO:1 or SEQ ID NO: 7.

As a protein containing substantially the same amino acid sequence as the amino acid sequence represented by SEQ ID NO: 1 or SEQ ID NO: 7, for example, a protein containing substantially the same amino acid sequence as the amino acid sequence represented by SEQ ID NO: 1 or SEQ ID NO: 7 and having substantially the same activity as that of a protein containing the amino acid sequence represented by SEQ ID NO: 1 or SEQ ID NO: 7 is preferred.

Specifically, the protein which has substantially the same amino acid sequence as that shown by SEQ ID NO: 1 or SEQ ID NO: 7 include proteins containing the amino acid sequence represented by SEQ ID NO: 12, etc.

The esterase activity referred to in the specification means an activity associated with hydrolysis of carboxylic acid esters, phosphoric acid esters or sulfuric acid esters, preferably an activity associated with hydrolysis of carboxylic acid esters, in particular fatty acid esters in particular. The carboxylic acid ester as a substrate may be a neutral fatty acid such as triacylglycerols, diacylglycerols, monoacylglycerols, etc., and a natural substrate such as sterol esters, e.g., cholesteryl esters, as well as a synthetic substrate such as p-nitrophenylbutyric acid ester, etc. The acyl group provided for the ester bond may be any acyl as long as the carbon atom number is 2 or more, and may be fluorescent or radioactive.

The esterase activity can be assayed based on publicly known methods, and e.g., determined based on the screening methods later described.

The proteins of the invention also include so-called muteins such as proteins containing (i) an amino acid sequence represented by SEQ ID NO: 1 or SEQ ID NO: 7, of which 1 or 2 more (preferably approximately 1 to 30, more preferably approximately 1 to 10 and most preferably several (1 to 5)) amino acids are deleted; (ii) an amino acid sequence represented by SEQ ID NO: 1 or SEQ ID NO: 7, to which 1 or 2 more (preferably approximately 1 to 30, more preferably approximately 1 to 10 and most preferably several (1 to 5)) amino acids are added; (iii) an amino acid sequence represented by SEQ ID NO: 1 or SEQ ID NO: 7, into which 1 or 2 more (preferably approximately 1 to 30, more preferably approximately 1 to 10 and most preferably several (1 to 5)) amino acids are inserted, (iv) an amino acid sequence represented by SEQ ID NO: 1 or SEQ ID NO: 7, in which 1 or 2 more (preferably approximately 1 to 30, more preferably approximately 1 to 10 and most preferably several (1 to 5)) amino acids are substituted by other amino acids; and (v) a combination of the above amino acid sequences.

Furthermore, the proteins of the invention include so-called muteins such as proteins containing (i) an amino acid sequence represented by SEQ ID NO: 12, of which 1 or 2 more (preferably approximately 1 to 30, more preferably approximately 1 to 10 and most preferably several (1 to 5)) amino acids are deleted; (ii) an amino acid sequence represented by SEQ ID NO: 12, to which 1 or 2 more (preferably approximately 1 to 30, more preferably approximately 1 to 10 and most preferably several (1 to 5)) amino acids are added; (iii) an amino acid sequence represented by SEQ ID NO: 12, into which 1 or 2 more (preferably approximately 1 to 30, more preferably approximately 1 to 10 and most preferably several (1 to 5)) amino acids are inserted, (iv) an amino acid sequence represented by SEQ ID NO: 12, in which 1 or 2 more (preferably approximately 1 to 30, more preferably approximately 1 to 10 and most preferably several (1 to 5)) amino acids are substituted by other amino acids; and (v) a combination of the above amino acid sequences.

Throughout the present specification, the proteins are represented in accordance with the conventional way of describing proteins, that is, the N-terminus (amino terminus) at the left hand and the C-terminus (carboxyl terminus) at the right hand. In the proteins of the invention including the protein containing the amino acid sequence shown by SEQ ID NO: 1, the C-terminus may be in the form of a carboxyl group (—COOH), a carboxylate (—COO$^-$), an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; and the like. In addition, pivaloyloxymethyl or the like which is used widely as an ester for oral administration may also be used.

Where the protein of the invention contains a carboxyl group (or a carboxylate) at a position other than the C-terminus, it may be amidated or esterified and such an amide or ester is also included within the protein of the invention. The ester group may be the same group as that described with respect to the above C-terminal group.

Furthermore, examples of the protein of the invention include variants of the above proteins, wherein the amino group at the N-terminus (e.g., methionine residue) of the protein is protected with a protecting group (e.g., a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains.

The partial peptides of the protein of the invention may be any partial peptides of the protein of the invention described above, preferably those having a similar activity as that of the protein of the invention described above (e.g., the esterase activity, preferably, the triglyceride degradation activity). For example, in the amino acid sequence which constitutes the protein of the invention, there are employed peptides having sequences of at least 20, preferably at least 50, more preferably at least 70, much more preferably at least about 100 and most preferably at least about 200 amino acids, which exhibit the esterase activity.

In the partial peptide of the protein of the invention, 1 or 2 more (preferably approximately 1 to 10, more preferably several (1 or 5)) amino acids may be deleted; 1 or 2 more (preferably approximately 1 to 20, more preferably approximately 1 to 10 and most preferably several (1 or 5)) amino acids may be added; or 1 or 2 more (preferably approximately 1 to 20, more preferably approximately 1 to 10 and most preferably several (1 or 5)), amino acids may be inserted; or 1 or 2 more (preferably approximately 1 to 10, more preferably several (1 or 5)) amino acids may be substituted by other amino acids.

Preferred partial peptides of the protein of the invention include:

(1) An amino acid sequence at the position of 184–198 or 204–217 in the amino acid sequence represented by SEQ ID NO: 1;

(2) An amino acid sequence at the position of 184–198 or 204–217 in the amino acid sequence represented by SEQ ID NO: 7;

(3) An amino acid sequence at the position of 116–130 or 204–217 in the amino acid sequence represented by SEQ ID NO: 12; and the like.

The partial peptide of the invention is usable as an antigen for producing the antibodies, and thus does not necessarily have the esterase activity. The partial peptides (1) to (3) described above and others are desired for the partial peptides used as the antigens to product the antibodies.

As the salts of the protein or its partial peptide of the invention, salts with physiologically acceptable acids (e.g., inorganic acids, organic acids) or with bases (e.g., alkaline metal salts) are employed, and physiologically acceptable acid addition salts are particularly preferred. Examples of such salts are salts with inorganic acids (e.g., hydrochloric acid, phosphoric acid, hydrobromic acid or sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The protein or its salts of the invention may be manufactured by publicly known methods used to purify proteins from the warm-blooded animal cells or tissues described above, or may be manufactured by culturing transformants containing DNAs encoding the proteins later described of the invention. The protein or its salts may also be manufactured by the peptide synthesis methods later described.

Where the protein or its salts are manufactured from warm-blooded animal tissues or cells, the warm-blooded animal tissues or cells are homogenized, then the protein or its salt is extracted with an acid or the like, and is isolated and purified from the extract obtained by a combination of chromatography techniques such as reversed phase chromatography, ion exchange chromatography, and the like.

To synthesize the protein of the invention or the partial peptide, or salts thereof, or amides thereof, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective protein according to various condensation methods publicly known. At the end of the reaction, the protein is excised from the resin and at the same time, the protecting groups are removed. Then, intramolecular disulfide bond-forming reaction is performed in a highly diluted solution to obtain the objective protein or amides thereof.

For condensation of the protected amino acids described above, a variety of activation reagents for protein synthesis may be used, but carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents used to activate the protected amino acids or condense with the resin may be chosen from solvents that are known to be usable for protein condensation reactions. Acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents are usable. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the protein, for example, the α-carboxyl group of the carboxy terminal amino acid is first protected by amidation; the peptide (protein) chain is then extended to amino group for a desired length. Thereafter, a protein in which only the protecting group of the N-terminal α-amino group has been eliminated from the protein and a protein in which only the protecting group of the C-terminal carboxyl group has been eliminated are manufactured. The two proteins are condensed in a mixture of the solvents described above. The details of the condensation reaction are the same as described above. After the protected protein obtained by the condensation is purified, all the protecting groups are eliminated by the method described above to give the desired crude protein. This crude protein is purified by various known purification means. Lyophilization of the major fraction gives the amide of the desired protein.

To prepare the esterified protein, for example, the α-carboxyl group of the carboxy terminal amino acid is condensed with a desired alcohol to prepare the amino acid ester, which is followed by procedure similar to the preparation of the amidated protein above to give the desired esterified protein.

The partial peptide of the invention or salts thereof can be manufactured by publicly known methods for peptide synthesis, or by cleaving the protein of the invention with an appropriate peptidase. For the methods for peptide synthesis, for example, either solid phase synthesis or liquid phase synthesis may be used. That is, the partial peptide or amino acids that can construct the partial peptide of the invention can be condensed with the remaining part of the partial peptide of the invention. Where the product contains protecting groups, these protecting groups are removed to give the desired peptide. Publicly known methods for condensation and elimination of the protecting groups are described in 1) to 5) below.

1) M. Bodanszky & M. A. Ondetti: Peptide Synthesis, Interscience Publishers, New York (1966)

2) Schroeder & Luebke: The Peptide, Academic Press, New York (1965)

3) Nobuo Izumiya, et al.: *Peptide Gosei-no-Kiso to Jikken* (Basics and experiments of peptide synthesis), published by Maruzen Co. (1975)

4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

5) Haruaki Yajima ed.: *Zoku Iyakuhin no Kaihatsu* (A sequel to Development of Pharmaceuticals), Vol. 14, Peptide Synthesis, published by Hirokawa Shoten After completion of the reaction, the partial peptide of the invention can be purified and isolated by a combination of conventional purification methods such as solvent extraction, distillation, column chromatography, liquid chromatography and recrystallization to give the partial peptide of the invention. When the partial peptide obtained by the above methods is in a free form, the peptide can be converted into an appropriate salt by a publicly known method; when the protein is obtained in a salt form, it can be converted into a free form or a different salt form by a publicly known method.

The polynucleotide encoding the protein of the invention may be any polynucleotide, so long as it contains the base sequence encoding the protein of the invention described above, and preferably the polynucleotide is a DNA. Such a DNA may be any one of genomic DNA, genomic DNA library, cDNA derived from the cells or tissues described above, cDNA library derived from the cells or tissues described above and synthetic DNA.

The vector to be used for the library may be any of bacteriophage, plasmid, cosmid, phagemid, and the like. In addition, the DNA can be amplified by reverse transcriptase polymerase chain reaction (hereinafter abbreviated as RT-PCR) with total RNA or mRNA fraction prepared from the above-described cells or tissues.

The DNA encoding the protein of the invention may be any one of, for example, (1) a DNA containing the base sequence represented by SEQ ID NO: 2, or a DNA having a base sequence hybridizable to the base sequence represented by SEQ ID NO: 2 under high stringent conditions and encoding a protein which has an activity substantially equivalent to the activity of the protein of the invention (e.g., the esterase activity, etc.), and (2) a DNA having the base sequence represented by SEQ ID NO: 8, or a DNA having a base sequence hybridizable to the base sequence represented by SEQ ID NO: 8 under high stringent conditions and encoding a protein which has an activity substantially equivalent to the activity of the protein of the invention.

Examples of the DNA that is hybridizable to the base sequence represented by SEQ ID NO: 2 or SEQ ID NO: 8 under high stringent conditions include a DNA having at least about 70% homology, preferably at least about 80% homology, more preferably at least about 90% homology and most preferably at least about 95% homology, to the base sequence represented by SEQ ID NO: 2 or SEQ ID NO: 8. Specific examples of the DNA include a DNA containing the base sequence represented by SEQ ID NO: 11, and the like.

The hybridization can be carried out by publicly known methods or by a modification thereof, for example, according to the method described in Molecular Cloning, 2nd Ed., J. Sambrook et al., Cold Spring Harbor Lab. Press, (1989). A commercially available library may also be used according to the instructions of the attached manufacturer's protocol. The hybridization can be carried out preferably under high stringent conditions.

The high stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration at about 19 mM at a temperature of about 65° C. are most preferred.

More specifically, for the DNA encoding the protein having the amino acid sequence represented by SEQ ID NO: 1, there may be employed a DNA having the base sequence represented by SEQ ID NO: 2, etc. and, a DNA having the base sequence represented by SEQ ID NO: 8, etc. may be used for the DNA encoding the protein having the amino acid sequence represented by SEQ ID NO: 7. For the DNA encoding the protein having the amino acid sequence represented by SEQ ID NO: 12, a DNA having the base sequence represented by SEQ ID NO: 11, etc. may be employed.

The polynucleotide encoding the partial peptide of the invention may be any DNA so long as it contains the base sequence encoding the partial peptide of the invention described above, and is preferably a DNA. The DNA may also be any of genomic DNA, genomic DNA library, cDNA derived from the cells and tissues described above, cDNA library derived from the cells and tissues described above and synthetic DNA.

The DNA encoding the partial peptide of the invention may be, for example, any one of (1) a DNA having a partial base sequence of the DNA having the base sequence represented by SEQ ID NO: 2, or a DNA having a partial base sequence of the DNA having a base sequence hybridizable to the base sequence represented by SEQ ID NO: 2 under high stringent conditions and encoding a protein which has the activity substantially equivalent to the activity of the protein of the invention, and (2) a DNA having a partial base sequence of the DNA having the base sequence represented by SEQ ID NO: 8, or a DNA having a partial base sequence of the DNA having a base sequence hybridizable to the base sequence represented by SEQ ID NO: 8 under high stringent conditions and encoding a protein which has the activity substantially equivalent to the activity of the protein of the invention, or the like. Specific examples of the DNA that is hybridizable to the base sequence represented by SEQ ID NO: 2 or SEQ ID NO: 8 include a DNA containing the base sequence represented by SEQ ID NO: 11, and the like.

Methods for the hybridization and the high stringent conditions that can be used are the same as described above.

For cloning of the DNA that completely encodes the protein of the invention or its partial peptide (hereinafter sometimes collectively referred to as the protein of the invention in the following description of cloning and expression of the DNA encoding these proteins or the like), the DNA may be either amplified by publicly known PCR using synthetic DNA primers containing a part of the base sequence of the protein of the invention, or the DNA inserted into an appropriate vector can be selected by hybridization with a labeled DNA fragment or synthetic DNA that encodes a part or the entire region of the protein of the invention. The hybridization can be carried out, for example, according to the method described in Molecular Cloning, 2nd (J. Sambrook et al., Cold Spring Harbor Lab. Press, 1989). The hybridization may also be performed using commercially available library in accordance with the protocol described in the attached instructions.

Conversion of the base sequence of DNA can be effected by publicly known methods such as the ODA-LAPCR method, the Gapped duplex method or the Kunkel method, or modifications thereof, by using publicly known kits available as Mutan™-super Express Km (TaKaRa Shuzo Co., Ltd.) or Mutan™-K (TaKaRa Shuzo Co., Ltd.), etc.

The cloned DNA encoding the protein of the invention can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector for the protein of the invention can be manufactured, for example, by (a) excising the desired DNA fragment from the DNA encoding the protein of the invention, (b) and then ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, HIV/LTR promoter, CMV promoter, HSV-TK promoter, etc.

Among them, CMV (cytomegalovirus) promoter or SRα promoter is preferably used. Where the host is bacteria of the genus *Escherichia*, preferred examples of the promoter include trp promoter, lac promoter, recA promoter, λPL promoter, lpp promoter, T7 promoter, etc. In the case of using bacteria of the genus *Bacillus* as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin promoter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo, G418 resistance), etc. In particular, when dhfr gene is used as the selection marker together with dhfr gene, selection can also be made on thymidine free media.

If necessary, a signal sequence that matches with a host is added to the N-terminus of the protein of the invention. Examples of the signal sequence that can be used are Pho A signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector bearing the DNA encoding the protein of the invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)), JA221 (Journal of Molecular Biology, 120, 517 (1978)], HB101 [Journal of Molecular Biology, 41, 459 (1969)), C600 (Genetics, 39, 440 (1954)], etc.

Examples of the bacteria belonging to the genus *Bacillus* include *Bacillus subtilis* MI114 [Gene, 24, 255 (1983)], 207–21 (Journal of Biochemistry, 95, 87 (1984)], etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, *Bombyx mori* N cell (BmN cell), etc. is used. Examples of the Sf cell which can be used are Sf9 cell (ATCC CRL1711) and Sf21 cell (both cells are described in Vaughn, J. L. et al., In Vivo, 13, 213–217 (1977).

As the insect, for example, a larva of *Bombyx mori* can be used [Maeda et al., Nature, 315, 592 (1985)].

Examples of animal cells include monkey cell COS-7, Vero, Chinese hamster cell CHO (hereinafter referred to as CHO cell), dhfr gene deficient Chinese hamster cell CHO (hereinafter simply referred to as CHO(dhfr⁻) cell), mouse L cell, mouse AtT-20, mouse myeloma cell, rat GH 3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979).

Yeast can be transformed, for example, by the method described in Methods in Enzymology, 194, 182–187 (1991) or Proc. Natl. Acad. Sci. U.S.A., 75, 1929 (1978), etc.

Insect cells or insects can be transformed, for example, according to the method described in Bio/Technology, 6, 47–55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263–267 (1995), published by Shujunsha, or Virology, 52, 456 (1973).

Thus, the transformant transformed with the expression vector containing the DNA encoding the protein can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extracts, vitamins, growth stimulsting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431–433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultivated generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20 to 35° C. for about 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)), RPMI 1640 medium (The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30 to 40° C. for about 15 to 60 hours and, if necessary, the culture can be aerated or agitated.

As described above, the protein of the invention can be produced in the cells, the cell membrane or outside of the cell of the transformant, etc.

The protein of the invention can be separated and purified from the culture described above by the following procedures.

When the protein of the invention is extracted from the culture or cells, after cultivation the bacteria or cell is collected by a publicly known method and suspended in an appropriate buffer. The bacteria or cell is then disrupted by publicly known methods such as ultrasonication, a treatment with lysozyme and/or freeze-thaw cycling, followed by centrifugation, filtration, etc. Thus, the crude extract of the protein or its partial peptide of the invention can be obtained. The buffer used for the procedures may contain a protein modifier such as urea or guanidine hydrochloride, or a surfactant such as Triton X-100™, etc. When the protein or its partial peptide of the invention is secreted in the culture broth, after completion of the cultivation the supernatant can be separated from the transformant or cell to collect the supernatant by publicly known methods.

The protein of the invention contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reversed phase high performance liquid chromatography, etc.; a method utilizing difference in isoelectric point such as isoelectrofocusing electrophoresis; and the like.

When the protein of the invention thus obtained is in a free form, it can be converted into the salt by publicly known methods or modifications thereof. On the other hand, when the protein is obtained in the form of a salt, it can be converted into the free form or in the form of a different salt by publicly known methods or modifications thereof.

The protein of the invention produced by the recombinant can be treated, prior to or after the purification, with an appropriate protein modifying enzyme so that the protein or partial peptide can be appropriately modified to partially remove a protein. Examples of the protein-modifying enzyme include trypsin, chymotrypsin, arginyl endopeptidase, protein kinase, glycosidase and the like.

The presence or activity of the thus produced protein of the invention or salts thereof can be determined by an enzyme immunoassay using a specific antibody, or by the amount of fatty acids liberated due to degradation of neutral lipids (the amount of enzymatic activity), or the like.

Antibodies to the protein of the invention, its partial peptide, or salts thereof, may be any of polyclonal antibodies and monoclonal antibodies, as long as they are capable of recognizing the protein of the invention, its partial peptide, or salts thereof.

The antibodies to the protein of the invention, its partial peptide, or salts thereof (hereinafter in the description of antibodies sometimes merely referred to as the protein of the invention) may be manufactured by publicly known methods for manufacturing antibodies or antisera, using as antigens the protein of the invention.

[Preparation of Monoclonal Antibody]

(a) Preparation of Monoclonal Antibody-producing Cells

The protein of the invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, mice, rats, sheep, goats and chickens, with the use of mice and rats being preferred.

In the preparation of monoclonal antibody-producing cells, a warm-blooded animal, e.g., mouse, immunized with an antigen wherein the antibody titer is noted is selected, then spleen or lymph node is collected after two to five days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled protein, which will be described later, with the antiserum followed by assaying the binding activity of the labeling agent bound to the antibody. The fusion may be carried out, for example, by the known method by Koehler and Milstein [Nature, 256, 495 (1975)]. Examples of the fusion promoter are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by culturing at 20 to 40° C., preferably at 30 to 37° C. for 1 to 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the protein (protein) as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the protein labeled with a radioactive substance or an enzyme and detecting the monoclonal antibody bound to the solid phase; etc.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody].

[Preparation of Polyclonal Antibody]

The polyclonal antibody of the invention can be manufactured by publicly known methods or modifications thereof. For example, a warm-blooded animal is immunized with an immunogen (protein of the invention as an antigen) per se, or a complex of immunogen and a carrier protein is formed and a warm-blooded animal is immunized with the complex in a manner similar to the method described above for the manufacture of monoclonal antibodies. The product containing the antibody to the protein of the invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester, activated ester reagents containing thiol group or dithiopyridyl group, and others are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every about 2 to 6 weeks about 3 to 10 times in total.

The polyclonal antibody can be collected from the blood, ascites, etc., preferably from the blood of warm-blooded animals immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described above.

Hereinafter the utilities of the protein of the invention or its partial peptide, or salts thereof (hereinafter sometimes collectively referred to as the protein, etc. of the invention); the DNA encoding the protein of the invention or its partial peptide (hereinafter sometimes collectively referred to as the DNA of the invention), and the antibody to the protein of the invention or its partial peptide, or salts thereof (hereinafter sometimes collectively referred to as the antibody of the invention).

[1] Agents for the Prevention/Treatment for Various Diseases with Which the Protein of the Invention is Associated Since the protein of the invention contributes to the degradation and control of neutral lipids (e.g., neutral fats and cholesteryl esters, etc.), and specifically has the triglyceride degradation activity, etc., any abnormality or deficiency in the DNA encoding the protein of the invention or a reduced expression level of the protein of the invention would develop a variety of diseases such as arteriosclerosis, hyperlipidemia, obesity, mellitus diabetes, etc.

Thus, the protein, etc. of the invention and the DNA of the invention can be used as pharmaceuticals such as prophylactic/therapeutic agents for various diseases such as arteriosclerosis, hyperlipidemia, obesity, mellitus diabetes, etc.

When a patient has a reduced level of, or deficient in the protein of the invention in his or her body, the DNA of the invention can provide its role sufficiently or properly for the patient, (a) by administering the DNA of the invention to the patient to express the protein, etc. of the invention in vivo, (b) by inserting the DNA of the invention into a cell, expressing the protein, etc. of the invention and then transplanting the cell to the patient, or (c) by administering the protein, etc. of the invention to the patient.

Where the DNA of the invention is used as the prophylactic/therapeutic agents described above, the DNA per se is administered directly to human or other warm-blooded animal; alternatively, the DNA is inserted into an appropriate vector such as retrovirus vector, adenovirus vector, adenovirus-associated virus vector, etc. and then administered to human or other warm-blooded animal in a conventional manner. The DNA of the invention may also be administered as naked DNA, or with physiologically acceptable carrier such as adjuvants to assist its uptake by gene gun or through a catheter such as a catheter with a hydrogel.

Where the protein, etc. of the invention is used as the aforesaid therapeutic/prophylactic agents, the protein is advantageously used on a purified level of at least 90%, preferably at least 95%, more preferably at least 98% and most preferably at least 99%.

The protein, etc. of the invention can be used orally, for example, in the form of tablets which may be sugar coated if necessary, capsules, elixirs, microcapsules etc., or parenterally in the form of injectable preparations such as a sterile solution and a suspension in water or with other pharmaceutically acceptable liquid. These preparations can be manufactured by mixing the protein, etc. of the invention with a physiologically acceptable carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80TM, HCO-50, etc.), or the like. Examples of the oily medium include sesame oil and soybean oil, which may also be used in combination with a dissolution aid such as benzyl benzoate and benzyl alcohol. The liquid for injection described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The vector in which the DNA of the invention is inserted may also be prepared into pharmaceutical preparations in a manner similar to the procedures above. Such preparations are generally used parenterally.

Since the thus obtained pharmaceutical preparation is safe and low toxic, the preparation can be administered to warm-blooded animals (e.g., human, rat, mouse, guinea pig, rabbit, bird, sheep, swine, bovine, horse, cat, dog, monkey, chimpanzee, etc.).

A dose of the protein, etc. of the invention varies depending on target disease, subject to be administered, route for administration, etc.; when the protein, etc. of the invention is orally administered for the purpose of treatment for, e.g., arteriosclerosis, the protein, etc. is administered to adult (as 60 kg body weight) normally in a daily dose of about 0.1 mg to about 100 mg, preferably about 1.0 to about 50 mg, and more preferably about 1.0 to about 20 mg. In parenteral administration, a single dose of the protein, etc. varies depending on subject to be administered, target disease, etc. but when the protein, etc. of the invention is administered to adult (as 60 kg body weight) in the form of injection for the purpose of treatment for arteriosclerosis, it is advantageous to administer the protein, etc. in a daily dose of about 0.01 to 30 mg, preferably about 0.1 to 20 mg, and more preferably about 0.1 to 10 mg. For other animal species, the corresponding dose as converted per 60 kg body weight can be administered.

[2] Screening of Drug Candidate Compounds for Disease

Since the protein, etc. of the invention possesses the esterase activity and especially has the triglyceride degradation activity, a compound or its salts that promotes the function of the protein, etc. of the invention (e.g., the esterase activity, etc.) can be used as drugs such as prophylactic/therapeutic agents for arteriosclerosis, hyperlipidemia, obesity, mellitus diabetes, etc. Also, the genes for the protein, etc. of the invention are specifically expressed in adipose tissues, and can thus be employed as drugs such as prophylactic/therapeutic agents for obesity.

Thus, the protein, etc. of the invention or the DNA of the invention can be used as probes for screening the compound or its salts that promote or inhibit the function of the protein, etc. of the invention.

That is, the present invention provides the method of screening a compound or its salts that promote or inhibit the function of the protein of the invention (e.g., the esterase activity, etc.), which comprises using the protein, its partial peptide, or salts thereof (hereinafter sometimes collectively referred to as the protein of the invention)of the invention. Specifically, the present invention provides, for example:

(1) a method of screening a compound or its salts that promote or inhibit the esterase activity of the protein of the invention, which comprises culturing a cell capable of expressing the gene of the protein of the invention in the presence of a test compound and measuring the amount of mRNA encoding the protein of the invention, by using a DNA encoding the protein of the invention, or its complementary DNA or its partial DNA; and more specifically, (2) a method of screening a compound or its salts that promote or inhibit the esterase activity of the protein of the invention, which comprises comparing (i) the amount of mRNA of the protein of the invention when a cell capable of expressing the gene of the protein of the invention is cultured, and (ii) the amount of mRNA of the protein of the invention when a cell capable of expressing the gene of the protein of the invention is cultured in the presence of a test compound.

Examples of the cell capable of expressing the gene of the protein of the invention are the aforesaid publicly known warm-blooded animal cells (preferably, adipocytes, macrophages, skeletal muscle cells), animal cells transformed by introducing the gene of the protein of the invention, etc. Such animal cells transformed by introducing the gene of the protein of the invention can be prepared by the methods described above.

Cultivation of the cell capable of expressing the gene for the protein of the invention can be carried out in a manner similar to publicly known methods for cultivating animal cells. As culture medium, there are employed, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The cell is usually cultivated at about 30 to 40° C. for about 15 to 60 hours and, if necessary, the culture can be aerated or agitated.

The comparison between the expression amounts of mRNA by the hybridization method can be carried out by publicly known methods or by modifications thereof, for example, according to the method described in Molecular Cloning, 2nd Ed. (J. Sambrook et al., Cold Spring Harbor Lab. Press, 1989).

Specifically, the amount of mRNA encoding the protein of the invention is determined in accordance with publicly known methods, by contacting the RNA extracted from the cell with the DNA encoding the gene for the protein of the invention, its complementary DNA or its partial DNA, and measuring the amount of mRNA bound to the DNA encoding the gene of the protein of the invention or its complementary DNA. The amount of mRNA bound to the complementary DNA to the DNA encoding the gene of the protein of the invention can be readily determined by labeling the complementary DNA to the DNA encoding the gene of the protein of the invention or its partial DNA with, e.g., a radioisotope, a dye, etc. Examples of the radioisotope are $^{32}P$, $^{3}H$, etc. and examples of the dye are fluorescent dyes such as fluorescein, FAM (manufactured by PE Biosystems), JOE (manufactured by PE Biosystems), TAMRA (manufactured by PE Biosystems), ROX (manufactured by PE Biosystems), Cy5 (manufactured by Amersham), Cy3 (manufactured by Amersham), etc.

The amount of mRNA encoding the protein of the invention can also be determined by converting RNA extracted from the cell into cDNA using a reverse transcriptase, and measuring the amount of cDNA amplified by PCR using as a primer the DNA encoding the gene of the protein of the invention or its complementary DNA or its partial DNA.

Examples of the complementary DNA to the gene DNA of the invention, which is used to determine the amount of mRNA encoding the protein of the invention, include a DNA (lower strand) having a complementary sequence to the gene DNA (upper strand) of the invention. Examples of the partial DNA of the gene DNA of the invention include base sequences composed of consecutive bases of approximately 10 to 2200, preferably approximately 10 to 300, and more preferably approximately 10 to 30, in the base sequence of the gene DNA encoding the protein of the invention. Examples of the partial DNA of the complementary DNA of the gene DNA of the invention include DNAs having a complementary sequence to the partial DNA of the DNA encoding the protein of the invention described above. That is, examples of the complementary DNA include DNAs having a complementary sequence to the base sequence composed of consecutive bases of approximately 10 to 2200, preferably approximately 10 to 300, and more preferably approximately 10 to 30, in the base sequence of the gene DNA encoding the protein of the invention.

Examples of the primers used for PCR are a DNA having the base sequence represented by SEQ ID NO: 5, a DNA having the base sequence represented by SEQ ID NO: 6, and the like.

In more detail, the mRNA level encoding the protein of the invention can be measured specifically by the following procedures.

(i) Normal or disease non-human mammal models (e.g., mice, rats, rabbits, sheep, swine, bovine, cats, dogs, monkeys, more specifically, obese mice, arteriosclerotic mice, arteriosclerotic rabbits, tumor-bearing mice, etc.) receive a drug (e.g., a hypotensive, anticancer, antiobestic or antihyperlipidemic drug, etc.) or physical stress (e.g., soaking stress, electric stress, light and darkness, low temperature, etc.) or the like, and the blood, specific organs (e.g., brain, liver, kidneys, etc.), or tissues or cells isolated from the organs are obtained after a given period of time.

The mRNA encoding the protein of the invention contained in the cells obtained is extracted from the cells, etc., for example, in a conventional manner, and quantified by means of, e.g., TaqManPCR, etc., or may also be analyzed by the northern blotting using publicly known methods.

(ii) Transformants that express the protein of the invention are prepared in accordance with the methods described above, and the mRNA encoding the protein of the invention can be quantified and analyzed as described above.

The test compound that increases the level of mRNA encoding the protein of the invention can be selected as a compound having an activity of promoting the expression of the gene for the protein of the invention.

Furthermore, the present invention provides:

(3) a method of screening a compound or its salts that promote the esterase activity of the protein of the invention, which comprises culturing cells (e.g., adipocytes, macrophages, skeletal muscle cells, etc.) transformed by the DNA, which are obtained by cloning a publicly known promoter or enhancer region from genomic DNA encoding the protein of the invention followed by ligation upstream a suitable reporter gene, in the presence of a test compound and detecting expression of the reporter gene in place of expression of the protein of the invention.

As the reporter gene, there are used, e.g., a dyed marker gene, etc., such as lacZ (β-galactosidase gene), etc.

By determining the amount of the reporter gene product (e.g., mRNA, protein) by publicly known methods, the test compound that increases the amount of the reporter gene product can be selected as a compound having an activity of promoting expression of the gene for the protein of the invention.

The cell can be cultured similarly by the publicly known animal cell culture described above.

The present invention further provides:

(4) a method of screening a compound or its salts having an activity that promote or inhibit the esterase activity of the protein of the invention, which comprises measuring the amount of neutral lipids produced (e.g., triglycerides, cholesteryl esters, etc.) (i) when the cell capable of producing the protein of the invention is cultivated in contact with an RI-labeled precursor (specific examples are fatty acids such as oleic acid, etc. or glycerol, labeled with $^3$H or $^{14}$C), and (ii) when the cell capable of producing the protein of the invention is cultivated in contact with an RI-labeled precursor and a test compound, by the method described in SEIKAGAKU BUNSEKI HO (Biochemical Analysis Technique; edited by H. Yuki, pp. 235–272, published by Nankodo, 1984), e.g., by thin layer chromatography, column chromatography, etc., and comparing (i) and (ii).

The cell can be cultured similarly by the publicly known animal cell culture described above.

The test compound that suppresses the amount of neutral lipids produced or increases the amount of the degradation products produced can be selected as a compound having the activity of promoting or inhibiting the expression of the gene of the protein of the invention.

The esterase activity of the protein, etc. of the invention can be assayed by publicly known methods, e.g., by the method described in Holm, C. and Osterlund, T., Methods in Molecular Biology, edited by M. H. Doolittle and K. Reue, 109, 109–121, or modifications thereof.

For example, the test compound that increases the esterase activity in the case of (ii) above by at least about 20%, preferably at least about 30% and more preferably at least about 50% as compared to the case of (i) can be selected as a compound that promotes the esterase activity of the protein, etc. of the invention, whereas the test compound that reduces the esterase activity in the case of (ii) above by at least about 20%, preferably at least about 30% and more preferably at least about 50% as compared to the case of (i) can be selected as a compound that inhibits the esterase activity of the protein, etc. of the invention.

Furthermore, the present invention provides:

(5) a method of screening a compound or its salts that promote or inhibit the esterase activity of the protein of the invention, which comprises culturing a cell capable of expressing the gene encoding the protein of the invention in the presence of a test compound and measuring the expression level of the protein of the invention, using the antibody to the protein of the invention; and more specifically, (6) a method of screening a compound or its salts that promote or inhibit the esterase activity of the protein of the invention, which comprises measuring (i) the expression level of the protein of the invention when a cell capable of expressing the gene encoding the protein of the invention is cultured, and (ii) the expression level of the protein of the invention when a cell capable of expressing the gene encoding the protein of the invention is cultured in the presence of a test compound, using the antibody to the protein of the invention, and comparing (i) and (ii).

The antibody to the protein of the invention can be manufactured by the methods described above. The cell can be cultured similarly by the publicly known animal cell culture described above. Also, the expression level of the protein of the invention can be quantified by the methods of quantifying the protein of the invention described in [3] below.

That is, more specifically, the present invention provides:

(7) a method of screening a compound or its salts that promote or inhibit the esterase activity of the protein of the invention, which comprises comparing the ratios of the labeled protein of the invention bound to the antibody (i) when the cell capable of expressing the gene encoding the protein of the invention is cultured and the antibody to the protein of the invention is competitively reacted with the resulting culture medium (test sample fluid) and a labeled form of the protein, etc. of the invention; and (ii) when the cell capable of expressing the gene encoding the protein of the invention is cultured in the presence of a test compound and the antibody to the protein of the invention is competitively reacted with the resulting culture medium (test sample fluid) and a labeled form of the protein, etc. of the invention; and, (8) a method of screening a compound or its salts that promote or inhibit the esterase activity of the protein of the invention, which comprises assaying the activity of a labeling agent on an insoluble carrier (i) when the cell capable of expressing the gene encoding the protein of the invention is cultured and the resulting culture medium (test sample fluid) is reacted simultaneously or sequentially with the antibody to the protein of the invention immobilized on a carrier and a labeled form of another antibody of the invention and (ii) when the cell capable of expressing the gene encoding the protein of the invention is cultured in the presence of a test compound and the resulting culture medium (test sample fluid) is reacted simultaneously or sequentially with the antibody to the protein of the invention immobilized on a carrier and a labeled form of another antibody of the invention.

In the method (8) described above, it is preferred that one antibody is capable of recognizing the N-terminal region of the protein, etc. of the invention, while another antibody is capable of reacting with the C-terminal region of the protein, etc. of the invention.

Examples of the test compound in the screening method described above include peptides, proteins, non-peptide compounds, synthetic compounds, fermentation products, cell extracts, vegetable extracts, animal tissue extracts, etc. and these compounds may be novel compounds or publicly known compounds.

The screening kit of the invention comprises the cell capable of expressing the gene of the protein of the invention, a labeled form of the protein of the invention, the antibody to the protein of the invention, etc.

The compound or its salts obtained using the screening method or screening kit of the present invention is the compound selected from the test compound described above, e. g., peptides, proteins, non-peptide compounds, synthetic compounds, fermentation products, cell extracts, vegetable extracts, animal tissue extracts, blood plasma, etc. and is the compound having the activity of promoting the function (e.g., the esterase activity, etc.) of the protein, etc. of the invention.

As the salts of the compound, the same salts as those of the protein of the invention described above are employed.

The compound having the activity of promoting the function (e.g., the esterase activity, etc.) of the protein, etc. of the invention can be used as drugs such as prophylactic/therapeutic agents for disease, e.g., arteriosclerosis, hyperlipidemia, obesity, mellitus diabetes, etc.

The compound having the activity of inhibiting the function (e.g., the esterase activity, etc.) of the protein, etc. of the invention can be used as drugs such as prophylactic/therapeutic agents for disease, e.g., obesity, etc.

When the compound obtained by the screening method or the screening kit of the invention is used as the prophylactic/therapeutic agent described above, such can be implemented in a conventional manner. For example, the compound can be administered orally or parenterally in the form of tablets, capsules, elixirs, microcapsules, sterile solutions, suspensions, etc., as in the pharmaceuticals comprising the protein, etc. of the invention.

Since the thus obtained pharmaceutical preparation is safe and low toxic, the preparation can be administered to, for example, warm-blooded animals (e.g., human, mouse, rat, rabbit, sheep, swine, bovine, horse, bird, cat, dog, monkey, chimpanzee, etc.).

A dose of the compound or its salts varies depending on its action, target disease, subject to be administered, route for administration, etc.; when the compound of promoting the function of the protein, etc. of the invention is orally administered for the treatment of, e.g., hyperlipidemia, the compound is administered to adult (as 60 kg body weight) normally in a daily dose of about 0.1 to 100 mg, preferably about 1.0 to 50 mg, and more preferably about 1.0 to 20 mg. In parenteral administration, a single dose varies depending on subject to be administered, target disease, etc. but when the compound that promotes the function of the protein, etc. of the invention is administered to adult (as 60 kg body weight) in the form of injection for the treatment of, e.g., hyperlipidemia, it is advantageous to administer the protein, etc. in a daily dose of about 0.01 to about 30 mg, preferably about 0.1 to about 20 mg, and more preferably about 0.1 to about 10 mg. For other animal species, the corresponding dose as converted per 60 kg body weight can be administered.

[3] Quantification for the Protein of the Invention, its Partial Peptide or Salts Thereof The antibody to the protein, etc. of the invention (hereinafter sometimes merely referred to as the antibody of the invention) is capable of specifically recognizing the protein, etc. of the invention and thus, can be used for a quantification of the protein of the invention in a test sample fluid, in particular, for quantification by sandwich immunoassay.

That is, the present invention provides:

(i) a method for quantification of the protein, etc. of the invention in a test sample fluid, which comprises competitively reacting the antibody of the invention with a test sample fluid and a labeled form of the protein, etc. of the invention, and measuring the ratio of the labeled protein, etc. of the invention; and, (ii) a method for quantification of the protein, etc. of the invention in a test sample fluid, which comprises reacting a test sample fluid simultaneously or sequentially with the antibody of the invention immobilized on a carrier and a labeled form of another antibody of the invention, and then measuring the activity of a labeling agent on the insoluble carrier.

In the method (ii) for quantification described above, it is preferred that one antibody is capable of recognizing the N-terminal region of the protein, etc. of the invention, while another antibody is capable of reacting the C-terminal region of the protein, etc. of the invention.

The monoclonal antibody to the protein, etc. of the invention (hereinafter sometimes referred to as the monoclonal antibody of the invention) may be used to assay the protein, etc. of the invention. Moreover, the protein of the invention can be detected by means of a tissue staining as well. For these purposes, the antibody molecule per se may be used or F(ab')$_2$, Fab' or Fab fractions of the antibody molecule may also be used.

There is no particular limitation for the assaying method using the antibody to the protein, etc. of the invention; any method may be used so far as it relates to a method in which the amount of antibody, antigen or antibody-antigen complex can be detected by a chemical or a physical means, depending on or corresponding to the amount of antigen (e.g., the amount of the protein) in a test sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of the labeling agent used in the assay method using the labeling substance are radioisotopes, enzymes, fluorescent substances and luminescent substances, etc. Examples of the radioisotope are [$^{125}$I], [$^{131}$I], [$^{3}$H], [$^{14}$C], etc. Preferred examples of the enzyme are those that are stable and have a high specific activity, which include β-galactosidase, β-glucosidase, alkaline phosphatase, peroxidase, malate dehydrogenase, etc. Examples of the fluorescent substance are fluorescamine, fluorescein isothiocyanate, etc. Examples of the luminescent substance are luminol, a luminol derivative, luciferin, lucigenin, etc. Furthermore, the biotin-avidin system may also be used for binding of an antibody or antigen to a labeling agent.

In the immobilization of antigens or antibodies, physical adsorption may be used. Alternatively, chemical binding that is conventionally used for immobilization of proteins or enzymes may be used as well. Examples of the carrier include insoluble polysaccharides such as agarose, dextran and cellulose; synthetic resins such as polystyrene, polyacrylamide, silicone, etc.; glass; etc.

In the sandwich method, a test sample fluid is reacted with an immobilized monoclonal antibody of the invention (primary reaction), then reacted with another labeled monoclonal antibody of the invention (secondary reaction) and the activity of the labeling agent on the insoluble carrier is assayed, whereby the amount of the protein of the invention in the test sample fluid can be quantified. The primary and secondary reactions may be carried out in a reversed order, simultaneously or sequentially with an interval. The type of the labeling agent and the method for immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the measurement sensitivity, etc.

In the method for assaying the protein, etc. of the invention by the sandwich method according to the present invention, preferred monoclonal antibodies of the present invention used for the primary and secondary reactions are antibodies, which binding sites to the protein, etc. of the invention are different from one another. Thus, the antibodies used in the primary and secondary reactions are those wherein, when the antibody used in the secondary reaction recognizes the C-terminal region of the protein, etc. of the invention, the antibody recognizing the site other than the C-terminal regions, e.g., recognizing the N-terminal region, is preferably used in the primary reaction.

The monoclonal antibody of the invention may be used in an assay system other than the sandwich method, such as a competitive method, an immunometric method, a nephrometry, etc.

In the competitive method, an antigen in a test sample fluid and a labeled antigen are competitively reacted with an antibody, then the unreacted labeled antigen (F) and the labeled antigen bound to the antibody (B) are separated (i.e., B/F separation) and the labeled amount of either B or F is measured to determine the amount of the antigen in the test sample fluid. In the reactions for such a method, there are a liquid phase method in which a soluble antibody is used as the antibody and the B/F separation is effected by polyethylene glycol while a second antibody to the antibody is used, and a solid phase method in which an immobilized antibody is used as the first antibody or a soluble antibody is used as the first antibody while an immobilized antibody is used as the second antibody.

In the immunometric method, an antigen in a test sample fluid and an immobilized antigen are competitively reacted with a given amount of a labeled antibody followed by separating the solid phase from the liquid phase; or an antigen in a test sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the test sample fluid.

In the nephrometry, the amount of insoluble sediment, which is produced as a result of the antigen-antibody reaction in a gel or in a solution, is measured. Even when the amount of an antigen in a test sample fluid is small and only a small amount of the sediment is obtained, a laser nephrometry utilizing laser scattering can be suitably used.

In applying each of those immunoassays to the assay method for the present invention, any special conditions or operations are not required to set forth. The assay system for the protein, etc. of the invention may be constructed in addition to conditions or operations conventionally used for each of the methods, taking the technical consideration of one skilled in the art into account-consideration. For the details of such conventional technical means, a variety of reviews, reference books, etc. may be referred. For example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (published by Academic Press); etc.) may be included.

As described above, the protein, etc. of the invention can be quantified with high sensitivity, using the antibody of the invention.

Furthermore, when a decreased level of the protein, etc. of the invention is detected by quantifying the level of the protein, etc. of the invention using the antibody of the invention, it can be diagnosed that diseases such as arteriosclerosis, hyperlipidemia, obesity, mellitus diabetes, etc. are involved or it is highly likely to suffer from these disease in the future.

The antibody of the present invention can be employed for detecting the protein, etc. of the invention which may be present in a test sample fluid such as a body fluid, a tissue, etc. The antibody can also be used for preparation of an antibody column for purification of the protein, etc. of the invention, detection of the protein of the invention in the fractions upon purification, and analysis of the behavior of the protein of the invention in the cells under investigation.

[4] Gene Diagnostic Agent

By using the DNA of the invention, e.g., as a probe, an abnormality of the DNA or mRNA encoding the protein of the invention or its partial peptide in warm-blooded animals (e.g., human, rat, mouse, guinea pig, rabbit, bird, sheep, swine, bovine, horse, cat, dog, monkey, chimpanzee, etc.) (gene abnormality) can be detected. Therefore, the DNA of the invention is useful as a gene diagnostic agent for the damage to the DNA or mRNA, its mutation, or its decreased expression, or increased expression or overexpression of the DNA or mRNA.

The gene diagnosis described above using the DNA of the invention can be performed by, for example, the publicly known northern hybridization assay or the PCR-SSCP assay (Genomics, 5, 874–879 (1989); Proceedings of the National Academy of Sciences of the United States of America, 86, 2766–2770 (1989)), etc.

For example, when decreased expression is detected by the northern hybridization or when mutation of the DNA is detected by the PCR-SSCP method, it can be diagnosed that highly likely to suffer from disease such as arteriosclerosis, hyperlipidemia, obesity, mellitus diabetes, etc.

[5] DNA Transgenic (Transfected) Animal

The present invention provides a non-human mammal bearing DNA encoding the protein of the invention, which is exogenous (hereinafter abbreviated as the exogenous DNA of the invention) or its variant DNA (sometimes simply referred to as the exogenous variant DNA of the invention).

Thus, the present invention provides:

(1) a non-human mammal bearing the exogenous DNA or its variant DNA;

(2) the mammal according to (1), wherein the non-human mammal is a rodent;

(3) the mammal according to (2), wherein the rodent is mouse or rat; and, (4) a recombinant vector bearing the exogenous DNA of the invention or its variant DNA and capable of expressing in a mammal.

The non-human mammal bearing the exogenous DNA of the invention or its variant DNA (hereinafter simply referred to as the DNA transgenic animal of the invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method etc. Also, it is possible to transfect the exogenous DNA of the invention into a somatic cell, a living organ, a tissue cell, or the like by the DNA transfection methods, and utilize the transformant for cell culture, tissue culture, etc. -In addition, these cells may be fused with the above-described germinal cell by a publicly known cell fusion method to prepare the transgenic animal of the invention.

Examples of the non-human mammal that can be used include bovine, swine, sheep, goat, rabbits, dogs, cats, guinea pigs, hamsters, mice, rats, etc. Among them, preferred are rodents, especially mice (e.g., C57B1/6 strain, DBA2 strain, etc. for a pure line and for a cross line, B6C3F1 strain, BDF1 strain B6D2F1 strain, BALB/c strain, ICR strain, etc.) or rats (Wistar, SD, etc.), since they are relatively short in ontogeny and life cycle from a standpoint of creating model animals for human disease.

"Mammals" in a recombinant vector that can be expressed in the mammals include the aforesaid non-human mammals and human.

The exogenous DNA of the invention refers to the DNA of the invention that is once isolated and extracted from mammals, not the DNA of the invention inherently possessed by the non-human mammals.

The mutant DNA of the invention includes mutants resulting from variation (e.g., mutation, etc.) in the base sequence of the original DNA of the invention, specifically DNAs resulting from base addition, deletion, substitution with other bases, etc. and further including abnormal DNA.

The abnormal DNA is intended to mean DNA that expresses the abnormal protein of the invention and exemplified by the DNA that expresses a protein for suppressing the function of the normal protein of the invention.

The exogenous DNA of the invention may be any one of those derived from a mammal of the same species as, or a different species from, the mammal as the target animal. In transfecting the DNA of the invention, it is generally advantageous to use the DNA as a DNA construct in which the DNA is ligated downstream a promoter capable of expressing the DNA in the target animal. For example, in the case of transfecting the human DNA of the invention, a DNA transgenic mammal that expresses the DNA of the invention to a high level, can be prepared by microinjecting a DNA construct (e.g., vector, etc.) ligated with the human DNA of the invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the invention highly homologous to the human DNA.

As expression vectors for the protein of the invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (1) promoters for DNA derived from viruses (e.g., simian virus, cytomegalovirus, Moloney leukemia virus, JC virus, breast cancer virus, poliovirus, etc.), and (2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), protein chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle a actin, preproencephalin A, vasopressin, etc. Among them, cytomegalovirus promoters, human protein elongation factor 1α (EF-1α) promoters, human and chicken β actin promoters, etc., which are capable of high expression in the whole body are preferred.

Preferably, the vectors described above have a sequence that terminates the transcription of the desired messenger RNA in the DNA transgenic animal (generally termed terminator); for example, a sequence of each DNA derived from viruses and various mammals, and SV40 terminator of the simian virus and the like are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal protein of the invention can be obtained using as a starting material the entire genomic DNA or its portion of liver, kidney, thyroid cell or fibroblast origin from various mammals (e.g., human, rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal protein obtained from the cells or tissues described above by point mutagenesis.

The translational region can be prepared by a conventional DNA engineering technique in which the DNA is ligated downstream the aforesaid promoter and if desired, upstream the translation termination site, as a DNA construct capable of being expressed in the transgenic animal.

The exogenous DNA of the invention is transfected at the fertilized egg cell stage in a manner such that the DNA is certainly present in all the germinal cells and somatic cells of the target mammal. The fact that the exogenous DNA of the invention is present in the germinal cells of the animal prepared by DNA transfection means that all offspring of the prepared animal will maintain the exogenous DNA of the invention in all of the germinal cells and somatic cells thereof. The offspring of the animal that inherits the exogenous DNA of the invention also have the exogenous DNA in all of the germinal cells and somatic cells thereof.

The non-human mammal in which the normal exogenous DNA of the invention has been transfected can be passaged as the DNA-bearing animal under ordinary rearing environment, by confirming that the exogenous DNA is stably retained by mating.

By the transfection of the exogenous DNA of the invention at the fertilized egg cell stage, the DNA is retained to be excess in all of the germinal and somatic cells. The fact that the exogenous DNA of the invention is excessively present in the germinal cells of the prepared animal after transfection means that the DNA of the invention is excessively present in all of the germinal cells and somatic cells thereof. The offspring of the animal that inherits the exogenous DNA of the invention have excessively the DNA of the invention in all of the germinal cells and somatic cells thereof.

By obtaining a homozygous animal having the transfected DNA in both of homologous chromosomes and mating a male and female of the animal, all offspring can be passaged to retain the DNA.

In a non-human mammal bearing the normal DNA of the invention, the normal DNA of the invention has expressed to a high level, and may eventually develop the hyperfunction of the protein of the invention by promoting the functions of endogenous normal DNA. Therefore, the animal can be utilized as a pathologic model animal for such a disease. Specifically, using the normal DNA transgenic animal of the invention, it is possible to elucidate the mechanism of the hyperfunction of the protein of the invention and the pathological mechanism of the disease associated with the protein of the invention and to determine how to treat the disease.

Furthermore, since a mammal transfected with the exogenous normal DNA of the invention exhibits an increasing symptom of the protein of the invention librated, the animal is usable for screening of therapeutic agents for the disease associated with the protein of the invention.

On the other hand, non-human mammal having the exogenous abnormal DNA of the invention can be passaged under normal breeding conditions as the DNA-bearing animal by confirming the stable retention of the exogenous DNA via crossing. Moreover, the objective exogenous DNA can be utilized as a starting material by inserting the DNA into the plasmid described above. The DNA construct with a promoter can be prepared by conventional DNA engineering techniques. The transfection of the abnormal DNA of the invention at the fertilized egg cell stage is preserved to be present in all of the germinal and somatic cells of the target mammal. The fact that the abnormal DNA of the invention is present in the germinal cells of the animal after DNA transfection means that all of the offspring of the animal prepared have the abnormal DNA of the invention in all of the germinal and somatic cells. Such an offspring which passaged the exogenous DNA of the invention retains the abnormal DNA of the invention in all of the germinal and somatic cells. By obtaining a homozygous animal having the transfected DNA in both of homologous chromosomes and mating a male and female of the animal, all offspring can be passaged to retain the DNA.

Since non-human mammal having the abnormal DNA of the invention may express the abnormal DNA of the invention at a high level, the animal may sometimes be the function inactivation type inadaptability to the protein of the invention by inhibiting the function of the endogenous normal DNA and can be utilized as its disease model animal. For example, using the abnormal DNA transgenic animal of the invention, it is possible to elucidate the mechanism of inadaptability to the protein of the invention and to perform to study a method for treatment of this disease.

More specifically, the transgenic animal of the invention expressing the abnormal DNA of the invention to a high level is also expected to serve as an experimental model to elucidate the mechanism of the functional inhibition (dominant negative effect) of normal protein by the abnormal protein of the invention in the function inactive type inadaptability to the protein of the invention.

A mammal bearing the abnormal exogenous DNA of the invention is also expected to serve for screening a candidate drug for the treatment of the function inactive type inadaptability to the protein of the invention, since the protein of the invention increases in such an animal in its free form.

Other potential applications of two kinds of the transgenic animals described above include:

(1) use as a cell source for tissue culture;

(2) elucidation of the relation to a protein that is specifically expressed or activated by the protein of the invention, by direct analysis of DNA or RNA in tissues of the DNA transgenic animal of the invention or by analysis of the protein tissues expressed by the DNA;

(3) research in the function of cells derived from tissues that are usually cultured only with difficulty, using cells in tissues bearing the DNA cultured by a standard tissue culture technique;

(4) screening a drug that enhances the functions of cells using the cells described in (3) above; and, (5) isolation and purification of the variant protein of the invention and preparation of an antibody thereto.

Furthermore, clinical conditions of a disease associated wit the protein of the invention, including the function inactive type inadaptability to the protein of the protein of the invention can be determined by using the DNA transgenic animal of the invention. Also, pathological findings on each organ in a disease model associated with the protein of the invention can be obtained in more detail, leading to the development of a new method for treatment as well as the research and therapy of any secondary diseases associated with the disease.

It is also possible to obtain a free cell, in which the DNA is transfected, by withdrawing each organ from the DNA transgenic animal of the invention, mincing the organ and degrading with a proteinase such as trypsin, etc., followed by establishing the line of culturing or cultured cells. Furthermore, the DNA transgenic animal of the invention can serve to identify cells capable of producing the protein of the invention, and to study in association with apoptosis, differentiation or propagation or on the mechanism of signal transduction in these properties to inspect any abnormality therein. Thus, the DNA transgenic animal of the invention can provide an effective research material for the protein of the invention and for elucidation of the function and effect thereof.

To develop a drug for the treatment of diseases associated with the protein of the invention, including the function inactive type inadaptability to the protein of the invention, using the DNA transgenic animal of the invention, an effective and rapid method for screening can be provided by using the method for inspection and the method for quantification, etc. described above. It is also possible to investigate and develop a method for DNA therapy for the treatment of diseases associated with the protein of the invention, using the DNA transgenic animal of the invention or a vector capable of expressing the exogenous DNA of the invention.

[6] Knockout Animal

The present invention provides a non-human mammal embryonic stem cell bearing the DNA of the invention inactivated and a non-human mammal deficient in expressing the DNA of the invention.

Thus, the present invention provides:

(1) a non-human embryonic stem cell in which the DNA of the invention is inactivated;

(2) the embryonic stem cell according to (1), wherein the DNA is inactivated by introducing a reporter gene (e.g., β-galactosidase gene derived from *Escherichia coli*);

(3) the embryonic stem cell according to (1), which is resistant to neomycin;

(4) the embryonic stem cell according to (1), wherein the non-human mammal is a rodent;

(5) the embryonic stem cell according to (4), wherein the rodent is mouse;

(6) a non-human mammal deficient in expressing the DNA of the invention, wherein the DNA of the invention is inactivated;

(7) the non-human mammal according to (5), wherein the DNA is inactivated by inserting a reporter gene (e.g., β-galactosidase derived from *Escherichia coli*) therein and the reporter gene is capable of being expressed under control of a promoter for the DNA of the invention;

(8) the non-human mammal according to (6), which is a rodent;

(9) the non-human mammal according to (8), wherein the rodent is mouse; and,

(10) a method of screening a compound that promotes or inhibits the promoter activity for the DNA of the invention, which comprises administering a test compound to the mammal of (7) and detecting expression of the reporter gene.

The non-human mammal embryonic stem cell in which the DNA of the invention is inactivated refers to a non-human mammal embryonic stem cell that suppresses the ability of the non-human mammal to express the DNA by artificially mutating the DNA of the invention, or the DNA has no substantial ability to express the protein of the invention (hereinafter sometimes referred to as the knockout DNA of the invention) by substantially inactivating the activities of the protein of the invention encoded by the DNA (hereinafter merely referred to as ES cell).

As the non-human mammal, the same examples as described above apply.

Techniques for artificially mutating the DNA of the invention include deletion of a part or all of the DNA sequence and insertion of or substitution with other DNA, by genetic engineering. By these variations, the knockout DNA of the invention may be prepared, for example, by shifting the reading frame of a codon or by disrupting the function of a promoter or exon.

Specifically, the non-human mammal embryonic stem cell in which the DNA of the invention is inactivated (hereinafter merely referred to as the ES cell with the DNA of the invention inactivated or the knockout ES cell of the invention) can be obtained by, for example, isolating the DNA of the invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter simply referred to as targeting vector). The thus-obtained ES cells to the Southern hybridization analysis with a DNA sequence on or near the DNA of the invention as a probe, or to PCR analysis with a DNA sequence on the targeting vector and another DNA sequence near the DNA of the invention which is not included in the targeting vector as primers, to select the knockout ES cell of the invention.

The parent ES cells to inactivate the DNA of the invention by homologous recombination, etc. may be of a strain already established as described above, or may be originally established in accordance with a modification of the publicly known method by Evans and Kaufman supra. For example, in the case of mouse ES cells, currently it is common practice to use ES cells of the 129 strain. However, since their immunological background is obscure, the C57BL/6 mouse or the BDF1 mouse (F1 hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The BDF1 mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1 to 10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

Where ES cells are allowed to reach a high density in mono-layers or to form cell aggregates in suspension under appropriate conditions, they will spontaneously differentiate to various cell types, for example, pariental and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the invention, which are obtained from the differentiated ES cells of the invention, are useful for studying the function of the protein of the invention cytologically or molecular biologically.

The non-human mammal deficient in expression of the DNA of the invention can be identified from a normal animal by measuring the mRNA amount in the subject animal by a publicly known method, and indirectly comparing the degrees of expression.

As the non-human mammal, the same examples supra apply.

With respect to the non-human mammal deficient in expression of the DNA of the invention, the DNA of the invention can be made knockout by transfecting a targeting vector, prepared as described above, to non-human mammal embryonic stem cells or oocytes thereof, and conducting homologous recombination in which a targeting vector DNA sequence, wherein the DNA of the invention is inactivated by the transfection, is replaced with the DNA of the invention on a chromosome of a non-human mammal embryonic stem cell or embryo thereof.

The knockout cells with the disrupted DNA of the invention can be identified by the Southern hybridization analysis using as a probe a DNA fragment on or near the DNA of the invention, or by the PCR analysis using as primers a DNA sequence on the targeting vector and another DNA sequence which is not included in the targeting vector. When non-human mammalian embryonic stem cells are used, a cell line wherein the DNA of the invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the invention and those having an artificially mutated locus of the DNA of the invention.

When some germ cells of the chimeric animal have a mutated locus of the DNA of the invention, an individual, which entire tissue is composed of cells having a mutated locus of the DNA of the invention can be selected from a series of offspring obtained by crossing between such a chimeric animal and a normal animal, e.g., by coat color identification, etc. The individuals thus obtained are normally deficient in heterozygous expression of the peptide of the invention. The individuals deficient in homozygous expression of the protein of the invention can be obtained from offspring of the intercross between the heterozygotes.

When an oocyte or egg cell is used, a DNA solution may be injected, e.g., to the prenucleus by microinjection thereby to obtain a transgenic non-human mammal having a targeting vector introduced in a chromosome thereof. From such transgenic non-human mammals, those having a mutation at the locus of the DNA of the invention can be obtained by selection based on homologous recombination.

As described above, individuals in which the DNA of the invention is rendered knockout permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell, in which the DNA of the invention is inactivated, is very useful for preparing a non-human mammal deficient in expression of the DNA of the invention.

Since the non-human mammal, in which the DNA of the invention is inactivated, lacks various biological activities derived from the protein of the invention, such an animal can be a disease model suspected of inactivated biological activities of the protein of the invention and thus, offers an effective study to investigate the causes for and therapy for these diseases.

[6a] Method of Screening a Compound Having a Therapeutic/Prophylactic Effect on Diseases Caused by Deficiency, Damages, etc. of the DNA of the Invention The non-human mammal deficient in expression of the DNA of the invention can be employed for screening of a compound having a therapeutic/prophylactic effect on diseases (e.g., arteriosclerosis, hyperlipidemia, obesity, mellitus diabetes, etc.) caused by deficiency, damages, etc. of the DNA of the invention.

That is, the present invention provides a method of screening a compound having a therapeutic/prophylactic effect on diseases caused by deficiency, damages, etc. of the DNA of the invention, which comprises administering a test compound to the non-human mammal deficient in expression of the DNA of the invention and observing and measuring a change occurred in the animal.

As the non-human mammal deficient in expression of the DNA of the invention that can be employed for the screening method, the same examples as given hereinabove apply.

Examples of the test compound include peptides, proteins, non-peptide compounds, synthetic compounds, fermentation products, cell extracts, plant extracts, animal tissue extracts, blood plasma and the like and these compounds may be novel compounds or publicly known compounds.

Specifically, the non-human mammal deficient in expression of the DNA of the invention is treated with a test compound, comparison is made with an intact animal for control and a change in each organ, tissue, disease conditions, etc. of the animal is used as an index to assess the therapeutic/prophylactic effects of the test compound.

For treating an animal to be tested with a test compound, for example, oral administration, intravenous injection, etc. are applied and the treatment can be appropriately selected depending upon conditions of the test animal, properties of the test compound, etc. Furthermore, a dose of the test compound to be administered can be selected depending on the administration route, nature of the test compound, etc.

For example, the non-human mammal deficient in expression of the DNA of the invention is subjected to a sugar loading treatment, a test compound is administered before or after the sugar loading treatment and, blood sugar level, body weight change, etc. of the animal is measured with passage of time, in the case of screening a compound having a therapeutic/prophylactic effect on artheriosclerosis.

In the screening method described above, when a test compound is administered to an animal to be tested and found to reduce the blood sugar level of the animal to at least about 10%, preferably at least about 30% and more preferably at least about 50%, the test compound can be selected to be a compound having a therapeutic and prophylactic effect on arteriosclerosis.

The compound obtained using the above screening method is a compound selected from the test compounds described above and exhibits a therapeutic and prophylactic effect on a disease (e.g., arteriosclerosis, etc.) caused by deficiencies, damages, etc. of the protein of the invention. Therefore, the compound can be employed as a safe and low toxic drug for the treatment and prevention of the disease. Furthermore, compounds derived from the compound obtained by the screening supra can be likewise employed.

The compound obtained by the screening method above may form salts, and may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A pharmaceutical comprising the compound obtained by the above screening method or salts thereof may be manufactured in a manner similar to the method for preparing the pharmaceutical comprising the protein of the invention described hereinabove. Since the pharmaceutical obtained is safe and low toxic, it can be administered to mammal (e.g., human, rat, mouse, guinea pig, rabbit, sheep, swine, bovine, horse, cat, dog, monkey, etc.).

A dose of the compound or its salt to be administered varies depending upon target disease, subject to be administered, route of administration, etc. in general; when the compound is orally administered for the purpose of treatment for, e.g., arteriosclerosis, the compound is administered to adult (as 60 kg body weight) in a daily dose of about 0.1 to 100 mg, preferably about 1.0 to 50 mg, more preferably about 1.0 to 20 mg. For parenteral administration to an adult (as 60 kg body weight), a single dose may vary depending upon subject to be administered, target disease, etc., but when the compound is administered in the form of an injectable preparation for the purpose of treatment for, e.g., arteriosclerosis, it is advantageous to administer the compound intravenously to an adult (as 60 kg body weight) in a daily dose of about 0.01 to 30 mg, preferably about 0.1 to 20 mg, more preferably about 0.1 to 10 mg, though the single dosage varies depending upon particular subject, particular disease, etc. As for other animals, the composition can be administered in the above amount with converting it into that for the body weight of 60 kg.

[6b] Method of Screening a Compound That Promotes or Inhibits the Activity of a Promoter to the DNA of the Invention The present invention provides a method of screening a compound or its salts that promote or inhibit the activity of a promoter to the DNA of the invention, which comprises administering a test compound to a non-human mammal deficient in expression of the DNA of the invention and detecting the expression of the reporter gene.

In the screening method above, the non-human mammal deficient in expression of the DNA of the invention is selected from the aforesaid non-human mammal deficient in expression of the DNA of the invention, as an animal in which the DNA of the invention is inactivated by introducing a reporter gene and the reporter gene is expressed under control of a promoter to the DNA of the invention.

The same examples of the test compound apply to specific compounds used for the screening.

As the reporter gene, the same specific examples apply to this screening method. Preferably employed are β-galactosidase (lacZ), soluble alkaline phosphatase gene, luciferase gene and the like.

Since a reporter gene is present under control of a promoter to the DNA of the invention in the non-human mammal deficient in expression of the DNA of the invention wherein the DNA of the invention is substituted with the reporter gene, the activity of the promoter can be detected by tracing expression of a substance encoded by the reporter gene.

When a part of the DNA region encoding the protein of the invention is substituted with, e.g., β-galactosidase gene (lacZ) derived from *Escherichia coli*, β-galactosidase is expressed in a tissue where the protein of the invention should originally be expressed, instead of the protein of the invention. Thus, the state of expression of the protein of the invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the protein of the invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening method above are compounds that are selected from the test compounds described above and that promote or inhibit the promoter activity to the DNA of the invention.

The compound obtained by the screening method above may form salts, and may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Since the compound or its salts that promote the promoter activity to the DNA of the present invention can promote the expression of the protein of the invention, they are useful as safe and low toxic drugs for the treatment/prevention of diseases such as arteriosclerosis, hyperlipidemia, obesity, mellitus diabetes, etc.

A pharmaceutical comprising the compound or its salts obtained by the screening method above may be manufactured in a manner similar to the method for preparing the pharmaceutical composition comprising the protein of the invention described hereinabove.

Since the pharmaceutical preparation thus obtained is safe and low toxic, it can be administered to a mammal (e.g., human, rat, mouse, guinea pig, rabbit, sheep, swine, bovine, horse, cat, dog, monkey, etc.).

A dose of the compound or salts thereof varies depending on target disease, subject to be administered, route for administration, etc.; when the compound that promotes the promoter activity to the DNA of the invention is orally administered for the purpose of treatment for, e.g., arteriosclerosis, the compound is administered to adult (as 60 kg body weight) normally in a daily dose of about 0.1 to 100 mg, preferably about 1.0 to 50 mg, more preferably about 1.0 to 20 mg. In parenteral administration, a single dose of the compound varies depending on subject to be administered, target disease, etc. but when the compound of promoting the promoter activity to the protein of the invention is administered to adult (as 60 kg body weight) in the form of injectable preparation for the purpose of treating arteriosclerosis, it is advantageous to administer the compound intravenously in a daily dose of about 0.01 to about 30 mg, preferably about 0.1 to about 20 mg, more preferably about 0.1 to about 10 mg. For other animal species, the corresponding dose as converted per 60 kg weight can be administered.

As stated above, the non-human mammal deficient in expression of the DNA of the present invention is extremely useful for screening the compound or its salt that promotes the promoter activity to the DNA of the invention and can greatly contribute to elucidation of causes for various diseases suspected of deficiency in expression of the DNA of the invention and for the development of prophylactic/therapeutic drug for these diseases.

Furthermore, a so-called transgenic animal (gene transferred animal) can be prepared by using DNA containing the promoter region of the protein of the invention, ligating genes encoding various proteins at the downstream and injecting the same into oocyte of an animal. It is then possible to synthesize the protein therein specifically and study its activity in vivo. When an appropriate reporter gene is ligated to the promoter site above and a cell line that expresses the gene is established, the resulting system can be utilized as the search system for a low molecular compound having the action of specifically promoting or inhibiting the in vivo productivity of the protein of the invention itself. Moreover, it is possible to find a novel cis-element and a transcription factor bound to the cis-element by analyzing the promoter portion.

In the specification and drawings, the codes of bases, amino acids, etc. are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |

-continued

| | |
|---|---|
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |

Substituents, protecting groups and reagents generally used in this specification are presented as the codes below.

| | |
|---|---|
| Me | methyl |
| Et | ethyl |
| Bu | butyl |
| Ph | phenyl |
| TC | thiazolidine-4(R)-carboxamido |
| Tos | p-toluenesulfonyl |
| CHO | formyl |
| Bzl | benzyl |
| Cl$_2$-Bzl | 2,6-dichlorobenzyl |
| Bom | benzyloxymethyl |
| Z | benzyloxycarbonyl |
| Cl—Z | 2-chlorobenzyloxycarbonyl |
| Br—Z | 2-bromobenzyl oxycarbonyl |
| Boc | t-butoxycarbonyl |
| DNP | dinitrophenol |
| Trt | trityl |
| Bum | t-butoxymethyl |
| Fmoc | N-9-fluorenyl methoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dichlorohexylcarbodiimide |

The sequence identification numbers in the sequence listing of the specification indicates the following sequence, respectively.

[SEQ ID NO: 1]

This shows the amino acid sequence of the protein of the invention LIP-1 T556 derived from human adipocyte.

[SEQ ID NO: 2]

This shows the base sequence of DNA encoding the protein of the invention derived from human adipocyte containing the amino acid sequence represented by SEQ ID NO: 1.

[SEQ ID NO: 3]

This shows the base sequence of synthetic primer used in EXAMPLE 1 for cloning of the DNA encoding the human-derived protein of the invention.

[SEQ ID NO: 4]

This shows the base sequence of synthetic primer used in EXAMPLE 1 for cloning of the DNA encoding the human-derived protein of the invention.

[SEQ ID NO: 5]

This shows the base sequence of synthetic primer used in EXAMPLE 2 for analysis of expression distribution in human tissues.

[SEQ ID NO: 6]

This shows the base sequence of synthetic primer used in EXAMPLE 2 for analysis of expression distribution in human tissues.

[SEQ ID NO: 7]

This shows the amino acid sequence of the protein of the invention LIP-1 T556 derived from human adipocyte.

[SEQ ID NO: 8]

This shows the base sequence of DNA encoding the protein of the invention derived from human adipocyte containing the amino acid sequence represented by SEQ ID NO: 7.

[SEQ ID NO: 9]

This shows the base sequence of synthetic primer used in EXAMPLE 3 for cloning of the DNA encoding the mouse-derived protein of the invention.

[SEQ ID NO: 10]

This shows the base sequence of synthetic primer used in EXAMPLE 3 for cloning of the DNA encoding the mouse-derived protein of the invention.

[SEQ ID NO: 11]

This shows the base sequence of DNA encoding MLIP-1, the mouse-derived protein of the invention.

[SEQ ID NO: 12]

This shows the amino acid sequence of mLIP-1, the mouse-derived protein of the invention.

Transformant *Escherichia coli* DH5α/pTB2122 obtained in EXAMPLE 1 later described has been on deposit with National Institute of Advanced Industrial Science and Technology, International Patent Organism Depositary (now-defunct Ministry of International Trade and Industry, Agency of Industrial Science and Technology, National Institute of Bioscience and Human Technology (NIBH)), located at Center No. 6, 1-1-1 Higashi, Tsukuba, Ibaraki, 305–8566, Japan, under Accession Number FERM BP-7277 since Aug. 21, 2000 and with the Institute for Fermentation, Osaka (IFO), located at 2-17-85, Juso-Honmachi, Yodogawa-ku, Osaka shi, Osaka, 532–8686, Japan, under Accession Number IFO 16463 since Aug. 8, 2000.

Also, transformant *Escherichia coli* DH5α/pTB2123 has been on deposit with the independent administrative agency, National Institute of Advanced Industrial Science and Technology, International Patent Organism Depositary (now-defunct Ministry of International Trade and Industry, Agency of Industrial Science and Technology, National Institute of Bioscience and Human Technology (NIBH)), located at Center No. 6, 1-1-1 Higashi, Tsukuba, Ibaraki, 305–8566, Japan, under Accession Number FERM BP-7278 since Aug. 21, 2000 and with the Institute for Fermentation, Osaka (IFO), located at 2-17-85,Juso-Honmachi, Yodogawa-ku, Osaka shi, Osaka, 532–8686, Japan, under Accession Number IFO 16464 since Aug. 8, 2000.

Further, transformant *Escherichia coli* DH5α/pTB2232 obtained in EXAMPLE 3 later described has been on deposit with the independent administrative agency, National Institute of Advanced Industrial Science and Technology, International Patent Organism Depositary (now-defunct Ministry of International Trade and Industry, Agency of Industrial Science and Technology, National Institute of Bioscience and Human Technology (NIBH)), located at Center No. 6, 1-1-1 Higashi, Tsukuba, Ibaraki, 305–8566, Japan, under Accession Number FERM BP-7630 since Jun. 14, 2001 and with the Institute for Fermentation, Osaka (IFO), located at 2-17-85, Juso-Honmachi, Yodogawa-ku, Osaka shi, Osaka, 532–8686, Japan, under Accession Number IFO 16649 since Jun. 5, 2001.

EXAMPLES

The present invention is described in detail below with reference to EXAMPLES, but not intended to limit the scope of the present invention thereto. The gene manipulation procedures using *Escherichia coli* were performed according to the methods described in the Molecular Cloning.

Example 1

Cloning of cDNA Encoding Human Adipocyte-derived Lipolytic Enzyme Proteins and Determination of the Base Sequences Using as a template Marathon-Ready cDNA (CLONTECH LABORATORIES, INC.) for human adipocytes, PCR was carried out using two primers, i.e., primer 1 (SEQ ID NO: 3) and primer 2 (SEQ ID NO: 4). The reaction solution for the reaction was composed of 1 μl of the above cDNA used as a template, 0.2 μl of Pfu Turbo DNA polymerase (STRATAGENE), 0.5 μM each of primer 1 (SEQ ID NO: 3) and primer 2 (SEQ ID NO: 4), 200 μM each of dNTPs, and 2 μl of the buffer attached to the enzyme to make the total volume 20 μl. PCR was carried out, after reacting at 94° C. for 1 minute, by repeating 30 times the cycle set to include 94° C. for 1 minute, 60° C. for 1 minute and 72° C. for 3 minutes, and finally extension was performed at 72° C. for 10 minutes. After adenine was protruded at the 3' end using ExTaq (TaKaRa Shuzo Co., Ltd.), the PCR product was subcloned to plasmid vector pCR2.1 (Invitrogen, Inc.) in accordance with the protocol of DNA Ligation Kit Ver. 2 (TaKaRa Shuzo Co., Ltd.). After the clones were introduced into *Escherichia coli* DH5α, the clones bearing cDNA were selected in LB agar medium supplemented with ampicillin. By sequencing analysis of the individual clones, two cDNA sequences (SEQ ID NO: 2 and SEQ ID NO: 8, respectively) encoding the novel neutral lipolytic enzyme proteins were acquired. The novel lipolytic enzyme proteins containing these amino acid sequences (SEQ ID NO: 1 and SEQ ID NO: 7, respectively) were named LIP-1 T556 and LIP-1 G556, respectively. In these two cDNA sequences, the 556th base was T or G and the 186th amino acid was Ser or Ala in these two amino acid sequences.

These transformants were named *Escherichia coli* DH5α/pTB2122 and pTB2123, respectively.

Example 2

Study of Expression Distribution in Human Tissues

Using Marathon-Ready cDNA (CLONTECH LABORATORIES, INC.) derived from 22 human tissues (adipose tissues, aorta, bone marrow, adult brain, large intestine, fetal brain, heart, kidney, leukocytes, liver, lung, mammary gland, ovary, pancreas, prostate gland, skeletal muscle, small intestine, spleen, testis, thymus gland, uterus and adrenal) as a template and two primers, i.e., primer 1 (SEQ ID NO: 5) and primer 2 (SEQ ID NO: 6), PCR was carried out. The reaction solution for the reaction was composed of 0.5 μl of the above cDNA used as a template, 0.1 μl of ExTaq (TaKaRa Shuzo Co., Ltd.), 0.5 μM each of primer 1 (SEQ ID NO: 5) and primer 2 (SEQ ID NO: 6), 200 μM each of dNTPs, and 2 μl of the buffer attached to the enzyme was added to make the total volume 20 μl. PCR was carried out, after reacting at 94° C. for 1 minute, by repeating 35 times the cycle set to include 94° C. for 30 seconds, 50° C. for 30 seconds and 72° C. for 2 minutes, and finally extension was performed at 72° C. for 5 minutes. Five microliters of the resulting reaction solution, was analyzed by 1.5% agarose gel electrophoresis.

The results of expression distribution of LIP-1 is shown in FIG. 1: wherein lanes 1, 2, 3, 4, 5, 6, 7, 8, 9, 10, 11, 12, 13, 14, 15, 16, 17, 18, 19, 20, 21 and 22 show adipose tissues, aorta, bone marrow, adult brain, large intestine, fetal brain, heart, kidney, leukocytes, liver, lung, mammary gland, ovary, pancreas, prostate gland, skeletal muscle, small intestine, spleen, testis, thymus gland, uterus and adrenal, respectively, and the molecular marker shows 100 bp marker (100 bases pair marker), and the triangle indicates that the position shown by the triangle is roughly the position where LIP-1 was expressed.

Example 3

Cloning of cDNA Encoding Mouse-derived Lipolytic Enzyme Proteins and Determination of Base Sequences Using mouse 17 day-embryo Marathon-Ready cDNA (CLONTECH LABORATORIES, INC.) as a template and two primers, i.e., primer 1 (SEQ ID NO: 9) and primer 2 (SEQ ID NO: 10), PCR was carried out. The reaction solution for the reaction was composed of 1 μl of the above cDNA used as a template, 0.2 μl of Pfu Turbo DNA polymerase (STRATAGENE), 1 μM each of primer 1 and primer 2, 200 μM each of dNTPs, 0.5 M GC-Melt (CLONTECH LABORATORIES, INC.), and 2 μl of the buffer attached to the enzyme to make the total volume 20 μl. PCR was carried out, after reacting at 94° C. for 1 minute, by repeating 30 times the cycle set to include 94° C. for 1 minute, 60° C. for 1 minute and 72° C. for 2 minutes, and finally extension was performed at 72° C. for 5 minutes. After adenine was protruded at the 3' end using ExTaq (TaKaRa Shuzo Co., Ltd.), the PCR product was subcloned to plasmid vector pCR2.1 (Invitrogen, Inc.) in accordance with the protocol of DNA Ligation Kit Ver. 2 (TaKaRa Shuzo Co., Ltd.). After the clones were introduced into *Escherichia coli* DH5α, the clones bearing cDNA were selected in LB agar medium supplemented with ampicillin. By sequencing analysis of the individual clones, the cDNA sequence (SEQ ID NO: 11) encoding the novel neutral lipolytic enzyme protein was acquired. The novel lipolytic enzyme protein containing the amino acid sequence (SEQ ID NO: 12) was named mLIP-1. This transformant was named *Escherichia coli* DH5α/pTB2232.

The amino acid sequence represented by SEQ ID NO: 12 was different in 83 amino acids from the amino acid sequence represented by SEQ ID NO: 1.

Example 4

Triglyceride Degradation Activity of Human and Mouse LIP-1 Gene Products

The cDNA encoding human LIP-1 T556, LIP-1 G556 or mLIP-1 (protein) was subcloned to expression vector pCI- Neo (Promega, Inc.) to obtain the respective recombinant plasmids hLIP-1T/pCI-Neo, hLIP-1G/pCI-Neo and mLIP-1/pCI-Neo. Using PolyFect reagent (Qiagen, Inc.), 2 µg each of these plasmid DNAs was transfected to HEK293 cells in a 6-well plate. After 48 hours, the cells were recovered and disrupted by ultrasonication (for 20 seconds) in 250 mM Sucrose—10 mM Tris HCl (pH 7.5)—1 mM EDTA buffer. The triglyceride degradation activity in the cell homogenate was assayed by the method of Osuga et al. [J. Osuga et al., Proc. Natl. Acad. Sci., 97, 787–792 (2000)], which method was modified in part.

That is, after reacting at 37° C. for 30 minutes in 40 µl of the reaction solution containing 105 µM tri[$^3$H]oleoyl glycerol (99.4 µCi/µmole, NEN, Inc.), 23.7 µM lecithin, 12.5 µM sodium taurocholate and 85 mM phosphate buffer (pH 7.0), 1.3 ml of methanol/chloroform/heptane (141:125:100) and 420 µl of 100 mM potassium borate buffer (pH 10.5) were added to the reaction mixture, followed by agitation and centrifugation. The radioactivity in the aqueous phase was then measured. The obtained radioactivity value was corrected by the cell protein level (measured by BCA Assay Kit of Pierece, Inc.), and compared, in which the active value for the control group (non-recombinant pCI-Neo vector-introduced cells) was made 100% (indicated by mean±standard error, N=3). The data was statistically treated using the Dunnett assay (*p<0.05, **p<0.01).

Figure 2:
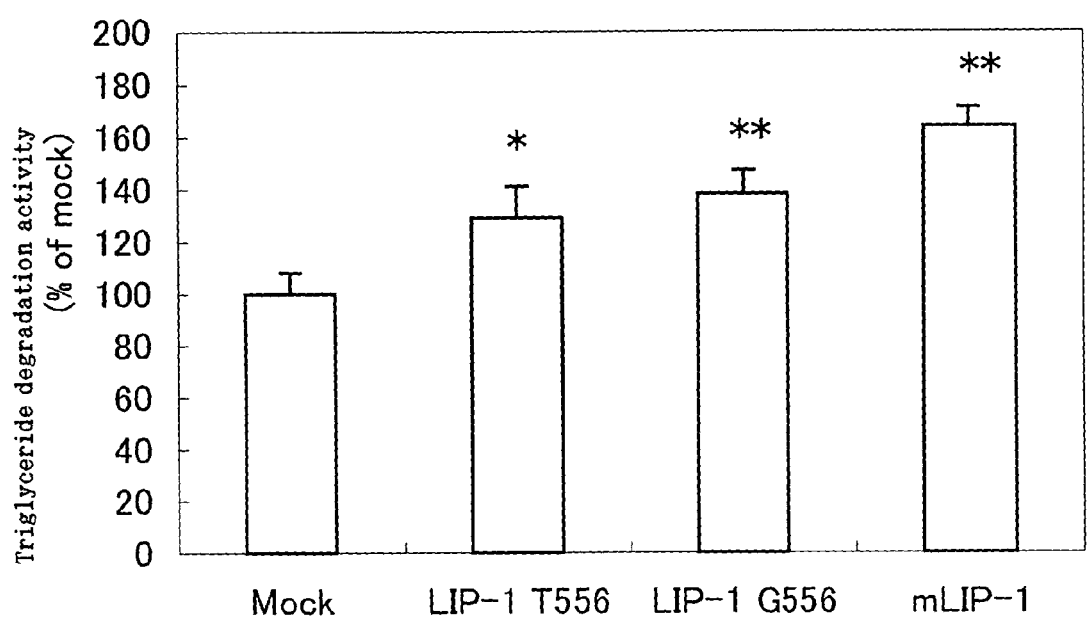
FIG. 2 shows the results of triglyceride degradation activity of cells wherein the respective genes have been introduced.

The results are shown in FIG. 2.

Based on the results, a significant increase of the triglyceride degradation activity was recognized in the cells transfected with LIP-1 T556, LIP-1 G556 and mLIP-1 genes. Thus, the results reveal that these gene products are novel triglyceride degradation enzymes.

INDUSTRIAL APPLICABILITY

The protein of the invention and the DNA encoding the same can be used as prophylactic/therapeutic agents for diseases such as arteriosclerosis, hyperlipidemia, obesity, mellitus diabetes, etc. Furthermore, the cell capable of expressing the protein of the invention or the gene of the protein of the invention is useful as a reagent for screening a compound or its salt that promotes the esterase activity of the protein of the invention. Moreover, the antibody to the protein of the invention is capable of specifically recognizing the protein of the invention, and can thus be used for quantification of the protein of the invention in a sample fluid, etc.

The invention claimed is:

1. An isolated protein or its salt, which consists of the amino acid sequence of SEQ ID NO: 1, having triglyceride degradation activity.

2. A method of screening a compound or its salt that promotes or inhibits the triglyceride degradation activity of the protein according to claim 1 or salt thereof, which comprises (i) contacting the protein of claim 1 or salt thereof, with a test compound (ii) detecting triglyceride degradation activity and comparing said activity with that measured in the absence of the test compound, and (iii) determining if said test compound inhibits or promotes triglyceride degradation activity.

3. A kit for screening a compound or its salt that promotes or inhibits the triglyceride degradation activity of the protein according to claim 1 or salt thereof, comprising the protein according to claim 1 or salt thereof.

* * * * *